(12) United States Patent
Smets et al.

(10) Patent No.: US 6,410,498 B1
(45) Date of Patent: Jun. 25, 2002

(54) LAUNDRY DETERGENT AND/OR FABRIC CARE COMPOSITIONS COMPRISING A MODIFIED TRANSFERASE

(75) Inventors: Johan Smets, Lubbeek (BE); Mary Vijayarani Barnabas, West Chester, OH (US); Michael Stanford Showell, Cincinnati, OH (US); Stanton Lane Boyer, Fairfield, OH (US); André Christian Convents, Cincinnati, OH (US)

(73) Assignee: Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/674,472

(22) PCT Filed: Apr. 30, 1999

(86) PCT No.: PCT/US99/09480

§ 371 (c)(1),
(2), (4) Date: Nov. 1, 2000

(87) PCT Pub. No.: WO99/57254

PCT Pub. Date: Nov. 11, 1999

(51) Int. Cl.⁷ ............. C11D 7/02; C11D 3/386; C12N 9/10; C12N 15/62; D06M 16/00
(52) U.S. Cl. ............ 510/392; 510/392; 510/320; 510/515; 510/530; 424/94.5; 435/193; 8/137
(58) Field of Search ............ 424/94.5; 510/392, 510/320, 305, 515, 530; 435/193; 8/137

(56) References Cited

U.S. PATENT DOCUMENTS

| | | | |
|---|---|---|---|
| 3,133,603 A | 5/1964 | Lagacherie et al. | 175/107 |
| 5,280,825 A | 1/1994 | Cholet | 166/311 |
| 5,484,016 A | 1/1996 | Surjaatmadja et al. | 166/104 |
| 5,518,379 A | 5/1996 | Harris et al. | 418/11 |

FOREIGN PATENT DOCUMENTS

| | | | |
|---|---|---|---|
| EP | 0481545 | 4/1994 | |
| WO | WO 91/10732 | 7/1991 | C12N/9/42 |
| WO | WO 94/24158 | 10/1994 | C07K/13/00 |
| WO | WO 97/28243 | 8/1997 | C11D/3/386 |
| WO | WO9728243 | * 8/1997 | 3/386 |
| WO | WO 97/28256 | 8/1997 | C12N/9/00 |
| WO | WO9728256 | * 8/1997 | 3/386 |

OTHER PUBLICATIONS

Evidence for a General Role for high–Affinity Non–Catalytic Cellulose Binding Domains in Microbial Plant Cell Wall Hydrolases (1994).

* cited by examiner

Primary Examiner—Lorna M. Douyon
Assistant Examiner—Eisa Elhilo
(74) Attorney, Agent, or Firm—C. Brant Cook; Kim W. Zerby; Steve W. Miller

(57) ABSTRACT

The present invention relates to a modified enzyme which comprises a catalytically active amino acid sequence of a transferase linked to an amino acid sequence comprising a Cellulose Binding Domain (CBD). The present invention further relates to laundry detergent and/or fabric care compositions comprising such modified enzyme, for improved fabric care and cleaning benefits.

38 Claims, No Drawings

LAUNDRY DETERGENT AND/OR FABRIC CARE COMPOSITIONS COMPRISING A MODIFIED TRANSFERASE

FIELD OF THE INVENTION

The present invention relates to laundry detergent and/or fabric care compositions comprising a modified enzyme which comprises a catalytically active amino acid sequence of a transferase, linked to an amino acid sequence comprising a Cellulose Binding Domain (CBD).

BACKGROUND OF THE INVENTION

Laundry detergent and/or fabric care compositions include nowadays a complex combination of active ingredients which fulfill certain specific needs: a surfactant system, enzymes providing cleaning and fabric care benefits, bleaching agents, a builder system, suds suppressors, soil-suspending agents, soil-release agents, optical brighteners, softening agents, dispersants, dye transfer inhibition compounds, abrasives, bactericides, perfumes, and their overall performance has indeed improved over the years.

However, the complex nature of everyday "body" soils typically found on pillow cases, T-shirts, collars and socks, provides a continuous thorough cleaning challenge for detergents. These soils are difficult to remove completely and often residues build up on fabric leading to dinginess and yellowing. In addition, removal by detergents of stains stemming from plants, wood, mud-clay based soil and fruits is one of the toughest cleaning challenges, in particular with the tendency to move to low wash temperatures and shorter washing cycles. These stains typically contain complex mixtures of fibrous material, based mainly on carbohydrates and their derivatives, fibre and cell wall components. Such stains are generally accompanied by amylose, sugars and their derivatives.

In recent years, consumer desirability for fabric conditioning compositions has risen. Fabric softening compositions impart several desirable properties to treated garments including softness and static control. Fabric softness of laundered garments is typically achieved by delivering a quaternary ammonium compound to the surface of the fabric. Consumer desirability for durable press fabric garments, particularly cotton fabric garments, has also risen. Durable press garments include those garments which resist wrinkling of the fabric both during wear and during the laundering process. Durable press garments can greatly decrease the hand work associated with laundering by eliminating ironing sometimes necessary to prevent wrinkling of the garment. However, in most commercially available durable press fabrics, the fabric's ability to resist wrinkling is reduced over time as the garment is repeatedly worn and laundered. Furthermore, coloured garments have a tendency to wear and show appearance losses. A portion of this colour loss may be attributed to abrasion in the laundering process, particularly in automatic washing machines and automatic laundry dryers. Moreover, tensile strength loss of fabric appears as an unavoidable result of mechanical/chemical action due to use/wearing or washing.

As indicated above, there is a continuous need for a laundry detergent composition which provides fabric cleaning and/or fabric stain removal, especially on body soils and plant based stains and/or fabric whiteness maintenance and/or fabric colour appearance and/or dye transfer inhibition.

In addition, there is a continuous need for a laundry detergent composition and/or fabric care composition, which can provide, refurbish or restore tensile strength, anti-wrinkle, anti-bobbling and anti-shrinkage properties to fabrics, as well as provide static control, fabric softness, colour appearance and fabric anti-wear properties and benefits.

The above objectives have been met by formulating laundry detergent and/or fabric care compositions comprising modified enzyme which comprises a catalytically active amino acid sequence of a transferase, linked to an amino acid sequence comprising a Cellulose Binding Domain (CBD).

Transferase enzymes have been described in the art: A process for producing saccharides of a definite chain length such as maltose and maltooligosaccharides in an isolated and highly pure form using saccharide chain transferase such as cyclodextrin glycosyl transferase or α-amylase, has been disclosed in EP 560 982 for pharmaceutical use. U.S. Pat. No. 5,516,689 describes an enzyme composition comprising transglucosidase and/or pectinase and a means of reducing the stickiness of honeydew contaminated cotton, to avoid severe problems during the milling of cotton. Microbial transglutaminases, their production and their use in a variety of industrial purposes have been described in WO96/06931. JP 7-107971 relates to a micro-organism belonging to the genus Bacillus and having the capacity to produce an alkali resistant cyclodextrin glucanotransferase for dishwashing applications wherein it demonstrates decomposition and removal of food soils and the produced cyclodextrin plays as a masking, desodorisation agent and it improves the sudsing properties and the emulsification of the soiling. Dishwashing detergent compositions containing cyclodextrin glucanotransferase with cleaning benefits and deodorising effect are described in JP 7-109488.

Enzymes linked to Cellulose Binding Domains are also described in the art: WO91/10732 novel derivatives of cellulase enzymes combining a core region derived from an endoglucanase producible by a strain of Bacillus spp., NICMB 40250 with a CBD derived from another cellulase enzyme or a combining a core region derived from another cellulase enzyme with a CBD derived from said endoglucanase, for improved binding properties. WO94/07998 describes cellulase variants of a cellulase classified in family 45, comprising a CBD, a Catalytically Active Domain (CAD) and a region linking the CBD to the CAD, wherein one or more amino acid residues have been added, deleted or substituted and/or another CBD is added at the opposite end of the CAD. WO95/16782 relates to the cloning and high level expression of novel truncated cellulase proteins or derivatives thereof in *Trichoderma longibrachiatum* comprising different core regions with several CBDs. WO97/01629 describes cellulolytic enzyme preparation wherein the mobility of the cellulase component may be reduced by adsorption to an insoluble or soluble carrier e.g. via the existing or newly introduced CBD. WO97/28243 describes a process for removal or bleaching or soiling or stains from cellulosic fabrics wherein the fabric is contacted in aqueous medium with a modified enzyme which comprises a catalytically active amino acid sequence of a non-cellulolytic enzyme selected from amylases, proteases, lipases, pectinases and oxidoreductases, linked to an amino acid sequence comprising a cellulose binding domain and a detergent composition comprising such modified enzyme and a surfactant.

Nevertheless, none of these documents discloses laundry detergent and/or fabric care compositions comprising a modified enzyme which comprises a catalytically active amino acid sequence of a transferase linked to an amino acid sequence comprising a Cellulose Binding Domain.

SUMMARY OF THE INVENTION

The present invention relates to a modified enzyme which comprises a catalytically active amino acid sequence of a transferase linked to an amino acid sequence comprising a Cellulose Binding Domain (CBD). In a second embodiment, the present invention relates to a laundry detergent and/or fabric care composition comprising such modified transferase enzyme, for improved fabric care and cleaning benefits. In a third embodiment, the present invention relates to a method comprising the step of contacting a fabric with the above laundry detergent and/or fabric care composition.

DETAILED DESCRIPTION OF THE INVENTION

The present invention relates to a modified enzyme (Enzyme hybrid) which comprises a catalytically active amino acid sequence of a transferase linked to an amino acid sequence comprising a Cellulose Binding Domain (CBD).

Transferase Enzyme and Substrates

Transferase enzymes catalyse the transfer of functional compounds to a range of substrates. Particularly, the transferase of the invention have the potential to transfer a chemical moiety, for example a methyl group or a glycosyl group, from a small substrate to form oligomeric molecules or elongate polymeric compounds. Using small substrates, the enzyme improves the properties of garments by binding functional groups like methyl, hydroxymethyl, formyl, carboxyl, aldehyde, ketone, acyl, amino and phosphorous functional groups and/or transferring glycosyl residues to the garment surface. The improved garments properties include tensile strength, anti-wrinkle, anti-bobbling and anti-shrinkage properties to fabrics, static control, fabric softness, colour appearance and fabric anti-wear properties and benefits. When the transferase level is high and the substrate concentration is low, the functional groups are transferred to water molecules providing cleaning benefits.

Without wishing to be bound by theory, it is believed that the addition of a cellulose binding domain to a transferase enzyme, allows a higher concentration of the transferase onto the fabric, i.e. a closer and/or more lasting contact, resulting in a more efficient enzymatic activity. Such modified transferases have an increased affinity (relative to unmodified enzyme) for binding to a cellulosic fabric or textile. It has been surprisingly found that said transferases when linked to a CBD provide improved excellent fabric cleaning and/or fabric stain removal, especially on body soils and plant based stains and/or fabric whiteness maintenance and/or fabric colour appearance and/or dye transfer inhibition. In addition, such modified enzymes provide enhanced fabric care, i.e. they provide, refurbish or restore tensile strength, anti-wrinkle, anti-bobbling and anti-shrinkage properties to fabrics, as well as provide enhanced static control, fabric softness, colour appearance and fabric anti-wear properties and benefits.

Suitable transferases for the present invention are represented by the EC 2.1 Transferring one-carbon groups enzymes, EC 2.2 Transferring aldehyde or ketone residues enzymes, EC 2.3 Acyltransferases, EC 2.4 Glycosyltransferases, EC 2.5 Transferring alkyl or aryl groups other than methyl groups enzymes, EC 2.6 Transferring nitrogenous groups enzymes and EC 2.7 Transferring phosphorus-containing groups enzymes.

Examples of suitable transferases are:

EC 2.1.1.15 Fatty acid O-methyltransferase
EC 2.1.1.18 Polysaccharide O-methyltransferase
EC 2.1.2.1 Glycine hydroxymethyltransferase
EC 2.1.2.4 Glycine formiminotransferase
EC 2.2.1.3 Formaldehyde transketolase
EC 2.3.1.3 Glucosamine N-acetyltransferase
EC 2.3.1.18 Galactoside acetyl transferase
EC 2.3.1.57 Diamine N-acetyltransferase
EC 2.3.1.75 Long-chain-alcohol O-fatty-acyltransferase
EC 2.3.1.79 Maltose O-acetyltransferase
EC 2.3.1.84 Alcohol O-fatty acetyltransferase
EC 2.3.1.88 Peptide α-N-acetyltransferase
EC 2.3.1.96 Glycoprotein N-palmitoyltransferase
EC 2.3.1.142 Glycoprotein O-fatty-acyltransferase
EC 2.5.1.10 Geranyltranstransferase
EC 2.5.1.20 Rubber cis-polypremylcistransferase
EC 2.6.1 Aminotransferase For specific applications, preferred transferases demonstrate some/most of their activity in the alkaline conditions, i.e., enzymes having an enzymatic activity of at least 10%, preferably at least 25%, more preferably at least 40% of their maximum activity at a pH ranging from 7 to 12, preferably 10.5. More preferred transferases are enzymes having their maximum activity at a pH ranging from 7 to 12, preferably 10.5. Other preferred transferase is a transferase having at least 50% of its maximum activity between 10° C. and 50° C.

Preferred transferases for the laundry detergent and/or fabric care compositions of the present invention are included in the acyltransferases (EC 2.3) and glycosyltransferases (EC 2.4) classes.

Of particular interest is the group of acyltransferases, especially the aminoacyl transferases (EC 2.3.2). These are enzymes transferring amino groups from a donor, generally an amino acid, to an acceptor. Even more preferred is the protein-glutamine γ-glutamyltransferase (EC 2.3.2.13), also available under the name transglutaminase. Without wishing to be bound by theory, it is believed that enzymatic crosslinking of amino acids, di/tri/poly-peptides and/or proteins will occur on the fabric, resulting in increased tensile strength and improved appearance. Moreover, hydrolysis by an aminoacyl transferase of said substrates present in the soils/stains, will provide cleaning benefits.

Of particular interest is also the group of glycosyltransferases. The general properties of these enzymes is to transfer a sugar from oligosaccharides to another carbohydrate as acceptor. Both hexosyltransferases and pentosyltransferases can be used in the invention. Glycosyltransferases catalyse both hydrolytic and transfer reactions in incubation with oligosaccharides. As a result of the enzymatic activity, oligosaccharides are converted into a new class of polysaccharides. It has been surprisingly found that glycosyltransferases linked to a cellulose binding domain improve the tensile strength and appearance of fabrics, e.g. reduce fabric wrinkles. Without wishing to be limited by any theory, it is indeed believed that due to the glycosyltransferase activity, oligosaccharides are bound to the cellulose polymers of cotton fabrics resulting in improved tensile strength and demonstrating appearance benefits especially after multiple wash cycles.

Without wishing to be bound by theory, the glycosyltransferase activity is believed to have 3 potential modes of action providing fabric care benefits:

Enzymatic stitching wherein the enzyme is thought to bind oligosaccharides to cellulose fibers with reduced tensile strength;

Enzymatic cross-linking wherein the glycosyltransferase is thought to bind cellulose fibers with reduced tensile strength together; and Enzymatic polymer linking wherein polymers are linked to cellulose fibers with reduced tensile strength;

In addition, in presence of a low level of substrate and a high level of glycosyltransferase, the glycosyl groups are transferred to water molecules thereby providing cleaning benefits.

For example, transglucosidase is an enzyme that catalyses both hydrolytic and transfer reactions in solutions containing α-D- gluco-oligosaccharides. As a result of the transglucosidase enzymatic reactions, the malto-oligosaccharides are converted to isomalto-oligosaccharides providing a new class of polysaccharides characterised by a higher proportion of saccharides linked by α-D-1,6 linkages from the non-reducing end.

These transglucosidases have been found to provide fabric care performance. It is believed that the improved tensile strength, the reduced wrinkling and better appearance are due to oligosaccharides bound to the cellulose polymers fibers of cotton.

Examples of suitable glycosyltransferases are galactosyl transferases and fructosyltransferases, such as 1,4-β-galactosyltransferase; 1,3-α-fructosyltransferase; 2,3-sialyl transferase; cyclodextrin glycosyltransferase; N-acetylgluco- or -galactosaminyltransferase; and EC 2.4.1.2 1,4-α-D-glucan: 1,6-α-D-glucan 6-α-D-glucosyltransferase EC 2.4.1.4 Sucrose: 1,4-α-D-glucan 4-α-D-glucosyltransferase EC 2.4.1.5 Sucrose:1,6-α-D-glucan 6-α-D-glucosyltransferase EC 2.4.1.9 Sucrose:2,1-β-D-fructan 1-β-D-fructosyltransferase EC 2.4.1.10 Sucrose:2,6-β-D-fructan 6-β-D-fructosyltransferase EC 2.4.1.11 UDP glucose:glycogen 4-α-D-glucosyltransferase EC 2.4.1.12 UDPglucose: 1,4-β-D-glucan 4-β-D-glucosyl transferase EC 2.4.1.13 UDPglucose:D-fructose 2-α-D-glucosyltransferase EC 2.4.1.16 UDP-N-acetylglucosamine: chitin 4-β-N-acetylglucosaminyl transferase EC 2.4.1.18 1,4-α-D-glucan:1,4-α-D-glucan 6-α-D-(1,4-α-D-glucano)-transferase EC 2.4.1.19 1,4-α-D-glucan 4-α-D-(1,4-α-D-glucano)-transferase (cyclizing)

EC 2.4.1.21 ADPglucose:1,4-α-D-glucan 4-α-Dglucosyltransferase

EC 2.4.1.24 1,4-α-D-glucan: 1,4-α-D-glucan(D-glucose) 6-α-D-glucosyltransferase

EC 2.4.1.25 1,4-α-D-glucan:1,4-α-D-glucan 4-α-D-glycosyl transferase

EC 2.4.1.29 GDPglucose:1,4-β-D-glucan 4-β-D-glucosyl transferase

EC 2.4.1.34 1,3-β-glucan synthetase

EC 2.4.1.35 UDPglucose:phenol β-D-glucosyltransferase

EC 2.4.1.49 1,4-β-D-oligo-D-glucan:orthophosphate α-d-glucosyltransferase

EC 2.4.1.67 1-α-D-galactosyl-myo-inositol:raffinosegalactosyl transferase

EC 2.4.1.71 UPDglucose:arylamine N-D-glucosyltransferase

EC 2.4.1.75 UDPgalacturonate β-D-galacturonosyl transferase

EC 2.4.1.82 1-α-D-galactosyl-myo-inositol:sucrose 6-α-D-galactosyltransferase

EC 2.4.1.90 UDPgalactose:N-acetyl-D-glucosamine 4-β-galactosyltransferase

EC 2.4.1.93 Inulin D-fructosyl-D-fructosyltransferase

EC 2.4.1.99 Sucrose: 1F-fructosyltransferase

EC 2.4. 1.100 1,2-β-D-fructan: 1,2-β-D-fructan 1-β-D-fructosyltransferase

EC 2.4.1.113 ADPglucose:protein 4-α-D-glucosyltransferase

EC 2.4.1.121 UDPglucose:indole-3-acetate β-D-glucosyltransferase

EC 2.4.1.125 Sucrose: 1,6-α-D-glucan 3(6)-α-D-glucosyl transferase

EC 2.4.1.140 Sucrose: 1,6(1,3)-α-D-glucan 6(3)-α-D-glucosyl transferase

EC 2.4.1.161 1,4-α-D-glucan: 1,4-α-D-glucan 4-α-D-glucosyltransferase

EC 2.4.1.168 UDPglucose: xyloglucan 1,4-β-D-glucosyl transferase

EC 2.4.1.169 UDP-D-xylose: xyloglucan 1,6-β-D-xylosyl transferase

EC 2.4.1.183 UDPglucose:α-D-(1,3)-glucan 3-α-D-glucosyltransferase

Of particular interest is EC 2.4.1.24 1,4-α-D-glucan: 1,4-a-D-glucan(D-glucose) 6-α-D-glucosyl transferase. A particulate member of this enzyme is commercially available under the name Transglucosidase L-500.

In addition to the glycosyltransferases discussed above, it has been found that mutant glycosyltransferases and/or mutant glycosidases, examples of which are described in PCT Application Publication No. WO 97/21822, its Canadian equivalent Canadian Patent No. 2,165,041, and its U.S. equivalent U.S. Pat. No. 5,716,812, all to S. G. Withers et al., improve the tensile strength and appearance of fabrics, e.g., reduce fabric wrinkles, enhance shape retention and reduce shrinkage. The mutant forms of glycosyl-transferases and/or glycosidases provide enzymatic stitching, enzymatic cross-linking and enzymatic polymer linking, as discussed above in greater detail. The mutant glycosyltransferases and/or mutant glycosidases only have one nucleophilic amino acid on the active site of the enzyme, rather than two, like non-mutated glycosyltransferases and/or non-mutated glycosidases, respectively. In other words, the mutant glycosyltransferases and/or mutant glycosidases are formed in which one of the normal nucleophilic amino acids within the active site has been changed to a non-nucleophilic amino acid. As a result, the mutant glycosyltransferases and/or mutant glycosidases only exhibit transferase activity; no hydrolytic activity is exhibited by the mutant glycosyltransferases nor the mutant glycosidases. Accordingly, unlike non-mutated glycosyltransferases and/or non-mutated glycosidases, the mutant glycosyltransferases and/or mutant glycosidases convert oligosaccharides into a new class of polysaccharides without the detrimental hydrolyzation of the new class of polysaccharides back into oligosaccharides or without water acting as acceptor for the transfer reaction.

These mutant glycosyltransferases and/or mutant glycosidases can be extracted from plant, yeast, bacteria or other organisms. The DNA of the mutant glycosyltransferases and/or mutant glycosidases can be cloned and expressed in bacteria, yeast or fungi and obtained in this way. These mutant glycosyltransferases and/or mutant glycosidases can be incorporated into heavy duty liquid detergents, heavy duty granular detergents, fabric care compositions, and the like. The novel characteristics and properties of the mutated glycosyltransferases and/or the mutated glycosidases make them highly suitable for use in laundry detergent and fabric care compositions because the absence of hydrolytic activity implies no loss in tensile strength of fabrics, even in the absence of donors in the transferase reaction. When mutant glycosyltransferases and/or mutant glycosidases are present in the compositions of the present invention, it is desirable that the saccharide concentration in the compositions is in the range of from about 0.01% to 30% by weight of the total composition, more preferably, 1% to 10% by weight of the total composition. Furthermore, the compositions of the present invention can have saccharides of high molecular weight added to the compositions to obtain the benefits discussed above.

Another enzyme that is of particular interest is endoxyloglucan transferase ("EXT"), which is described in J. Plant Res. 108, 137–148, 1995 by Nishitani, Kagoma University, and now called "EXGT" in Int. Review of Cytology, Vol. 173, p. 157, 1997 by Nishitani, Kagoma University and the xyloglucan endotransglycosylase ("XET") which is described in Novo Nordisk patent application WO97/23683. Like the mutant glycosyltransferases discussed above, this endoxylo-glucan transferase improves the tensile strength and appearance of fabrics, e.g., reduce fabric wrinkles, enhance shape retention and reduce shrinkage. The endoxyloglucan transferase stitch cellulose fibrils. These stitching properties of the enzyme on cellulose fibrils delivers the above mentioned benefits. Endoxyloglucan transferase is responsible for rejoining intermicrofibrillar xyloglucan chains, the xyloglucan chains between cellulosic microfibrils during the formation of plant cell walls. By rejoining the cellulosic microfibrils through xyloglucan linkages, the cellulose structure acquires improved strength of the fibers. Since the structure of fabrics is of cellulosic nature, the enzyme has a stitching activity on the microfibrils. Also shape retention, anti-shrinkage and anti-wrinkle benefits can be explained by the stitching properties of the enzyme.

Endoxyloglucan transferase differs in activity from xyloglucan endotransglycosylase ("XET transferase"), which is described in WO 97/23683 to Novo Nordisk A/S. The difference being that the xyloglucan endotransglycosylase shows both transferase activity and hydrolase activity. In contrast, endoxyloglucan transferase only shows transferase activity. No hydrolase activity is shown by endoxyloglucan transferase. Accordingly, unlike xyloglucan endotransglycosylase, the endoxyloglucan transferase converts oligosaccharides into a new class of polysaccharides without the detrimental hydrolyzation of the new class of polysaccharides back into oligosaccharides. Furthermore, the endoxyloglucan transferase exhibits strict donor specificity for high Mr (molecular weight) xyloglucan polymers and does not act on xyloglucan oligomers. The novel characteristics and properties of endoxyloglucan transferase make it highly suitable for use in laundry detergent and fabric care compositions because the absence of hydrolytic activity implies no loss in tensile strength of fabrics, even in the absence of donors in the transferase reaction. Furthermore, lower levels of substrate donor can be used. Without desiring to be limited, it is believed that high benefits can be obtained even in the absence of a donor substrate if the endoxyloglucan transferase uses xyloglucans of the primary wall of the cotton fiber within fabrics. Endoxyloglucan transferase can be extracted from plants and other organisms. Endoxyloglucan transferase can be obtained from a large number of plants including, but not limited to; *A. thaliana* and *V. angularis*. Alternatively, the DNA of the enzyme can be cloned and expressed in bacteria, yeast or fungi and obtained in this way. The endoxyloglucan transferase can be incorporated into heavy duty liquid detergents, heavy duty granular detergents, fabric care compositions, and the like.

When endoxyloglucan transferase is present in the compositions of the present invention, it is desirable that the xyloglucan concentration in the compositions is in the range of from about 0.01% to 30% by weight of the total composition, more preferably, 1% to 10% by weight of the total composition. Furthermore, the compositions of the present invention can have xyloglucan polymers of high molecular weight added to the compositions to obtain the benefits discussed above.

Yet another enzyme that is of particular interest is cyclomaltodextrin glucanotransferase ("CGT-ase") (EC 2.4.1.19), which is commercially available from Amano and Novo Nordisk A/S. Covalent linking of carbohydrates, oligo and polysaccharides to cotton surfaces, such as fabrics, with a transferase delivers benefits such as anti-wrinkling, color maintenance, dye fixation and soil repulsion. Covalent linkage of glucose units to the cellulose surface versus a physical absorption of polymers, which are produced by the transferase in situ (or others), make the observed benefits durable. Cyclomaltodextrin glucanotransferase is a transferase that exhibits several different actions on starch. It produces from starch $\alpha$, $\beta$, and $\gamma$ cyclodextrins, hydrolyzes starch and cross links starch. In these types of reactions, $\alpha$ sugars are both donor and acceptor for the transferase reaction. Up to now, it was not clear if these transferase enzymes could covalently link sugar units to cotton. Surprisingly, it has been found that cyclomaltodextrin glucanotransferase can covalently link glucose units from $\alpha$-cyclodextrine to the cotton surfaces of fabrics at the non-reducing end of the cellulose polymers. Accordingly, cyclomaltodextrin glucanotransferase has the ability to make the benefits discussed above more durable. As discussed above, it is known that covalently linking cellulose polymers with cross-linking agents delivers benefits to fabrics, such as anti-wrinkle benefits, but anti-wrinkle benefits can also be obtained by a physical absorption of polymers on the cotton surface. This physical absorption of polymers on the cotton surface can now be made more durable since one of the polymer units is covalently linked to the cotton surface by the action of cyclomaltodextrin glucanotransferase. Since these more durable benefits are produced enzymatically, the covalent linking occurs at a much lower temperature, thus, much lower temperatures as compared to conventional wash cycles are feasible in the wash cycle. In addition, conventional cross-linking chemicals (some of them are potentially toxic), which are used in the textile industry, are not applicable at the lower temperatures in the wash cycle. Other benefits, such as dye fixation and improved soil release, are obtained through the covalent incorporation of cationic or anionic glucose units to the cotton surface. Accordingly, the use of cyclomaltodextrin glucanotransferase in laundry detergent and fabric care compositions provides improved anti-wrinkle, shape retention, anti-shrinkage, dye fixation, soil repulsion and tensile strength benefits for fabrics. The cyclomaltodextrin glucanotransferase can be incorporated into heavy duty liquid detergents, heavy duty granular detergents, fabric care compositions, and the like. When cyclomaltodextrin glucanotransferase is present in the compositions of the present invention, it is desirable that the starch concentration in the compositions is in the range of from about 0.01% to 30% by weight of the total composition, more preferably, 1% to 10% by weight of the total composition. Furthermore, the compositions of the present invention can have cyclodextrins or types of starch and sucrose added to the compositions to obtain the benefits discussed above.

Yet still another group of enzymes that is of particular interest are glucansucrases, of which dextransucrase (EC 2.4.1.5) and glycosyltransferases, are examples. Other glucansucrases that are suitable for use in the compositions described herein include, but are not limited to, various dextransucrases, alternansucrase and levansucrase, which is commercially available from Genencor. Dextransucrase enzymes can be obtained from any suitable source known in the art, and are used in conjunction with appropriate substrates (sucrose +/−maltose). Dextransucrase catalyzes transfer reactions of glycosyl residues from one polysaccharide to another. As a result of dextransucrase reactions, high molecular weight dextrans are produce on fabric surfaces. In dextrans, glucose residues are linked by 1–6-α linkages. Modification of cotton fiber with carbohydrates, oligo and polysaccharides, delivers benefits such as anti-wrinkling, color maintenance, dye fixation and soil repulsion. The durability of these benefits may require covalent linkage of the oligosaccharides. It has been found that dextransucrase can bind oligosaccharides to cellulose polymers in cotton. As a result of this binding via the transfer reactions catalyzed by the dextransucrase, improved fabric appearance benefits are provided i.e., improved anti-wrinkling, shape retention, anti-shrinkage, dye fixation, soil repulsion and tensile strength benefits. When the reaction products are bound (may or may not be a covalent linkage) to cotton, they modify the cotton surface and fibrils, which in turn delivers the fabric care benefits discussed above. Dextransucrase with sucrose also provides improved whiteness benefits (dyes from other color garments are not deposited on white fabrics). The dextransucrase/sucrose combination forms high molecular weight dextran (and smaller oligomers when other saccharides such as maltose, cellobiose, etc., are present). Furthermore, it has been found that the deposition efficiency of reaction products on the fabrics is high, and that the reaction products are not all washed off in the following wash cycle.

When glucansucrase is present in the compositions of the present invention, it is desirable that the substrate (typically sucrose or other disaccharides) concentration in the compositions is in the range of from about 0.01% to 30% by weight of the total composition, more preferably, 1% to 10% by weight of the total composition. Furthermore, the compositions of the present invention can have smaller polysaccharides such as sucrose, maltose, maltdextrins, cellosaccharides, and types of starch added to the compositions to obtain the benefits discussed above.

These modified transferase enzymes are preferably incorporated into the laundry detergent and/or fabric care compositions in accordance with the invention at a level of from 0.0001% to 10%, more preferably from 0.0005% to 5%, most preferred from 0.001% to 1% pure modified enzyme by weight of the total composition.

The fabric care and/or cleaning benefits can be obtained by the laundry and/or fabric care compositions of the present invention in presence or absence of the corresponding natural enzymatic substrate. In general, the first part of the enzyme name indicates the substrate for the enzyme reaction and the second part is the acceptor to which the group is transferred. The substrate of the transferase enzyme can be the fabric fibre itself, stains and/or soils, added in any treatment including pre- or post-treatment from the textile industry and/or from any washing and/or fabric care process, and/or added together with the transferase-containing composition.

Examples of substrates for some of the transferases listed above are: S-adenosyl-L-methionine, 5,10-methylenetetrahydrofolate or formiminotetra-hydrofolate (hydroxymethyl or formyl group transfer to glycine), formaldehyde, acetyl Co A, methyl-a,w-diamine, palmityl Co A, geranoyl di phosphate.

In particular, the substrate for the aminoacyl transferases is an amino containing compound such as an amino acid, a di/tri/polypeptide and/or a protein.

Among the glycosyltransferases, though the transferring group is a glycosyl residue, the specifics of the substrate for each enzyme is derived from the first part of the name. Especially for the glycosyltransferases, the natural substrate could be any alpha-glucosyl saccharide chosen from amylaceous substances in a dimer, oligomer and/or polymer. Examples are preferably different forms of starch (gelatinized, liquefied, solubilized), partial starch hydrolysate, more preferably malto-oligosaccharides, and most preferably maltose. Of interest are also substituted starch/sugar substrates, containing methylation and carboxylation substitution. Alternatively, the following substrates could be used for the mentioned glycosyltransferases: dextrins, sucrose, raffinose, fructosyl polymers, UDP glucose, xyloglucan, GDP glucose, arylamine, UDP galacturonate, ADP glucose, indole-3-acetate, a-D-glucans, UDP-xylan.

The transferase-substrates are preferably incorporated into the compositions in accordance with the invention at a level of from 0.01% to 30%, more preferably from 0.1% to 20%, most preferably from 1% to 10% by weight of the total composition.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein/genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach and/or chelant stability, catalytic activity and the like, of the enzyme variant is tailored to suit the particular fabric conditioning and/or cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing calcium binding sites to increase chelant stability.

The catalytically active amino acid sequence of the transferase enzyme may comprise or consist of the whole of—or substantially the whole of—the full amino acid sequence of the mature enzyme in question, or it may consist of a portion of the full sequence which retains substantially the same catalytic (enzymatic) properties as the full sequence.

Modified enzymes (enzyme hybrids) of the type in question, as well as detailed descriptions of the preparation and purification thereof, are known in the art [see, e.g., WO90/00609, WO94/24158 and WO95/16782, as well as Greenwood et al., *Biotechnology and Bioengineering* 44 (1994) pp. 1295–1305]. The production of enzymes hybrid is given in WO91/10732 wherein novel derivatives of cellulase enzymes combining a core region derived from a Bacillus NICB 40250 endoglucanase with a CBD derived from another cellulase enzyme or combining a core region derived from another cellulase enzyme with a CBD derived from a Bacillus NICB 40250 endoglucanase, are constructed. WO95/16782 describes the combinations of different core regions with several CBD and the cloning and high level expression of these novel truncated cellulase proteins or derivatives thereof, in *Trichoderma longibrachiatum*.

They may, e.g., be prepared by transforming into a host cell a DNA construct comprising at least a fragment of DNA encoding the cellulose-binding domain ligated, with or without a linker, to a DNA sequence encoding the enzyme of interest, and growing the transformed host cell to express the fused gene. One relevant, but non-limiting, type of recombinant product (enzyme hybrid) obtainable in this matter—often referred to in the art as a "fusion protein"—may be described by one of the following general formulae:

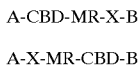

A-CBD-MR-X-B

A-X-MR-CBD-B

In the latter formulae, CBD is an amino acid sequence comprising at least the cellulose-binding domain (CBD) per se. MR (the middle region; a linking region) may be a bond, or a linking group comprising from 1 to about 100 amino acid residues, in particular of from 2 to 40 amino acid residues, e.g. from 2 to 15 amino acid residues. MR may, in principle, alternatively be a non-amino-acid linker (See below). X is an amino acid sequence comprising the above-mentioned, catalytically (enzymatically) active sequence of amino acid residues of a polypeptide encoded by a DNA sequence encoding the transferase enzyme of interest. The moieties A and B are independently optional. When present, a moiety A or B constitutes a terminal extension of a CBD or X moiety, and normally comprises one or more amino acid residues.

It will thus, inter alia, be apparent from the above that a CBD in an enzyme hybrid of the type in question may be positioned C-terminally, N-terminally or internally in the enzyme hybrid. Correspondingly, an X moiety in an enzyme hybrid of the type in question may be positioned N-terminally, C-terminally, or internally in the enzyme hybrid.

Enzyme hybrids of interest in the context of the invention include enzyme hybrids which comprise more than one CBD, e.g. such that two or more CBDs are linked directly to each other, or are separated from one another by means of spacer or linker sequences (consisting typically of a sequence of amino acid residues of appropriate length). Two CBDs in an enzyme hybrid of the type in question may, for example, also be separated from one another by means of an -MR-X- moiety as defined above. One or more cellulose binding domain can be linked to the N-terminal and/or C-terminal parts of the cellulase core region. Any part of a CBD can be selected, modified, truncated etc.

Preferably, attention will be paid in the construction of enzyme hybrids of the type in question to the stability towards proteolytic degradation. Two- and multi-domain proteins are particularly susceptible towards proteolytic cleavage of linker regions connecting the domains. Proteases causing such cleavage may, for example, be subtilisins, which are known to often exhibit broad substrate specificities [see, e.g.: Grøn et al., *Biochemistry* 31 (1992), pp. 6011–6018; Teplyakov et al., *Protein Engineering* 5 (1992), pp. 413–420]. Glycosylation of linker residues in eukaryotes is one Nature's ways of preventing proteolytic degradation. Another is to employ amino acids which are less favoured by the surrounding proteases. The length of the linker also plays a role in relation to accessibility by proteases. Which "solution" is optimal depends on the environment in which the enzyme hybrid is to function. When constructing new enzyme hybrid molecules, preferably attention will be paid to the linker stability.

Plasmids

Preparation of plasmids capable of expressing fusion proteins having the amino acid sequences derived from fragments of more than one polypeptide is well known in the art (see, for example, WO 90/00609 and WO 95/16782). The expression cassette may be included within a replication system for episomal maintenance in an appropriate cellular host or may be provided without a replication system, where it may become integrated into the host genome. The DNA may be introduced into the host in accordance with known techniques such as transformation, microinjection or the like.

Once the fused gene has been introduced into the appropriate host, the host may be grown to express the fused gene. Normally it is desirable additionally to add a signal sequence which provides for secretion of the fused gene. Typical examples of useful genes are:

1) Signal sequence—(pro-peptide)—carbohydrate-binding domain—linker—enzyme sequence of interest, or 2) Signal sequence—(pro-peptide)—enzyme sequence of interest—linker—carbohydrate-binding domain, in which the pro-peptide sequence normally contains 5–100, e.g. 5–25, amino acid residues. The recombinant product may be glycosylated or non-glycosylated.

Cellulose Binding Domain (CBD)

In the present context, the terms "amino acid sequence comprising a CBD or Cellulose Binding Domain or CBD" are intended to indicate an amino acid sequence capable of effecting binding of the cellulase to a cellulosic substrate (e.g. as described in P. Kraulis et al., Determination of the three-dimensional structure of the C terminal domain of cellobiohydrolase I from *Trichoderma reesei*. A study using nuclear magnetic resonance and hybrid distance geometry-dynamically simulated annealing. Biochemistry 28:7241–7257, 1989). The classification and properties of cellulose binding domains are presented in P. Tomme et al., in the symposium "Enzymatic degradation of insoluble polysaccharides" (ACS Symposium Series 618, edited by J. N. Saddler and M. H. Penner, ACS, 1995).

Cellulose-binding (and other carbohydrate-binding) domains are polypeptide amino acid sequences which occur as integral parts of large polypeptides or proteins consisting of two or more polypeptide amino acid sequence regions, especially in hydrolytic enzymes (hydrolases) which typically comprise a catalytic domain containing the active site for substrate hydrolysis and a carbohydrate-binding domain for binding to the carbohydrate substrate in question. Such enzymes can comprise more than one catalytic domain and one, two or three carbohydrate-binding domains, and they may further comprise one or more polypeptide amino acid sequence regions linking the carbohydrate-binding domain(s) with the catalytic domain(s), a region of the latter type usually being denoted a "linker".

Examples of hydrolytic enzymes comprising a cellulose-binding domain are cellulase, xylanases, mannanases, arabinofuranosidases, acetylesterases and chitinases. "Cellulose-binding domains" have also been found in algae, e.g. in the red alga porphyra purpurea in the form of a non-hydrolytic polysaccharide-binding protein [see P. Tomme et al., *Cellulose-binding domains—Classification* and *Properties in Enzymatic Degradation of Insoluble Carbohydrates,* John N. Saddler and Michael H. Penner (Eds.), ACS Symposium Series, No. 618 (1996)]. However, most of the known CBDs (which are classified and referred to by P. Tomme et al. (op. cit.) as "cellulose-binding domains"] derive from cellulases and xylanases.

In the present context, the term "cellulose-binding domain" is intended to be understood in the same manner as in the latter reference (P. Tomme et al., op. cit. ) The P. Tomme et al. reference classifies more than 120 "cellulose-binding domains" into 10 families (I–X) which may have different functions or roles in connection with the mechanism of substrate binding. However, it is to be anticipated that new family representatives and additional families will appear in the future.

In proteins/polypeptides in which CBDs occur (e.g. enzymes, typically hydrolytic enzymes such as cellulases), a CBD may be located at the N or C terminus or at an internal position.

The part of a polypeptide or protein (e.g. hydrolytic enzyme) which constitutes a CBD per se typically consists of more than about 30 and less than about 250 amino acid residues. For example, those CBDs listed and classified in Family I in accordance with P. Tomme et al. (op. cit.) consist of 33–37 amino acid residues, those listed and classified in Family IIa consist of 95–108 amino acid residues, those listed and classified in Family VI consist of 85–92 amino acid residues, whilst one CBD (derived from a cellulase from *Clostridium thermocellum*) listed and classified in Family VII consists of 240 amino acid residues. Accordingly, the molecular weight of an amino acid sequence constituting a CBD per se will typically be in the range of from about 4 kD to about 40 kD, and usually below about 35 kD.

Cellulose binding domains can be produced by recombinant techniques as described in H. Stålbrand et al., Applied and Environmental Microbiology, March 1995, pp. 1090–1097; E. Brun et al., (1995) Eur. J. Biochem. 231, pp. 142–148; J. B. Coutinho et al., (1992) Molecular Microbiology 6(9), pp. 1243–1252

In order to isolate a cellulose binding domain of, e.g. a cellulase, several genetic engineering approaches may be used. One method uses restriction enzyme to remove a portion of the gene and then to fuse the remaining gene-vector fragment in frame to obtain a mutated gene that encodes a protein truncated for a particular gene fragment. Another method involves the use of exonucleases such as Ba113 to systematically delete nucleotides either externally from the 5' and the 3' ends of the DNA or internally from a restricted gap within the gene. These gene-deletion methods result in a mutated gene encoding a shortened gene molecule whose expression product may then be evaluated for substrate-binding (e.g. cellulose-binding) ability. Appropriate substrates for evaluating the binding ability include cellulosic materials such as Avicel™ and cotton fibres. Other methods include the use of a selective or specific protease capable of cleaving a CBD, e.g. a terminal CBD, from the remainder of the polypeptide chain of the protein in question.

As already indicated (vide supra), once a nucleotide sequence encoding the substrate-binding (carbohydrate-binding) region has been identified, either as cDNA or chromosomal DNA, it may then be manipulated in a variety of ways to fuse it to a DNA sequence encoding the enzyme or enzymatically active amino acid sequence of interest. The DNA fragment encoding the carbohydrate-binding amino acid sequence, and the DNA encoding the enzyme or enzymatically active amino acid sequence of interest are then ligated with or without a linker. The resulting ligated DNA may then be manipulated in a variety of ways to achieve expression. Preferred microbial expression hosts include certain Aspergillus species (e.g. *A. niger* or *A. oryzae*), Bacillus species, and organisms such as *Escherichia coli* or *Saccharomyces cerevisiae*.

Preferred CBDs for the purpose of the present invention are selected from the group consisting of: CBDs CBHII from *Trichoderma reesei,* CBDs CenC, CenA and Cex from *Cellulomonas fimi,* CBD CBHI from *Trichoderma reesei,* CBD Cellulozome from *Clostridium cellulovorans,* CBD E3 from *Thermonospora fusca,* CBD-dimer from *Clostridium stecorarium* (NCIMB11754) XynA, CBD from *Bacillus agaradherens* (NCIMB40482) and/or CBD family 45 from *Humicola insolens.* More preferred CBDs for the purpose of the present invention are the CBD CenC from *Cellulomonas fimi,* CBD Cellulozome from *Clostridium cellulovorans* and/or the CBD originating from the fungal *Humicola Insolens* cellulase sold under the tradename "Carezyme" by Novo Nordisk A/S. Carezyme is an endoglucanase from family 45, derived from *Humicola insolens* DSM1800, having a molecular weight of about 43 kDa and exhibiting cellulolytic activity Linking Region The term "linker" or "linking region" or "Middle region—MR" is intended to indicate a region that might adjoin the CBD and connect it to the catalytically active amino acid sequence of the transferase enzyme. When present, this linking can be achieved chemically or by recombinant techniques.

An example of the recombinant technique describing the expression of an enzyme with the CBD of different origin is described in S. Karita et al., (1996) Journal of Fermentation and Bioengineering, Vol. 81, No. 6, pp. 553–556. Preferred linking regions are amino acid linking regions (peptides), some examples thereof are described in N. R. Gilkes et al., Microbiol. Rev. 55, 1991, pp. 303–315. The linking region can comprise from 1 to about 100 amino acid residues, in particular of from 2 to 40 amino acid residues, e.g. from 2 to 15 amino acid residues. As stated above, it is preferred to use amino acids which are less favoured by the surrounding proteases. Suitable amino acid linking regions are the *Humicola insolens* family 45 cellulase linker, the NifA gene of *Klebsiella pneumoniae*—CiP linker, the *E. coli* OmpA gene-CiP linker, the E3 cellulase *Thermonospora fusca* linker and the CenA cellulase linker; preferably the *Humicola insolens* family 45 cellulase linker and the E3 cellulase *Thermomonospora fusca* linker.

Non amino acid/proteinic compounds, referred to as "non-amino acid" can also be used for the linking of the catalytically active amino acid sequence to the CBD:

1) Suitable non-amino acid linking regions are the polyethylene glycol derivatives described in the Shearwater polymers, Inc. catalog of January 1996, such as the nucleophilic PEGs, the carboxyl PEGs, the electrophilically activated PEGs, the sulfhydryl-selective PEGs, the heterofunctional PEGs, the biotin PEGs, the vinyl derivatives, the PEG silanes and the PEG phospholipids. In particular, suitable non-amino acid linking regions are the heterofunctional PEG, (X-PEG-Y) polymers from Shearwater such as PEG(NPC)2, PEG- (NH2)2, t-BOC-NH-PEG-NH2, t-BOC-NH-PEG-CO2NHS, OH-PEG-NH-tBOC, FMOC-NH-PEG-CO2NHS or PEG(NPC)$_2$ MW 3400 from Sigma, glutaric dialdehyde 50 wt % solution in water from Aldrich, disuccinimidyl suberate (DSS) form Sigma, γ-maleimidobutyric acid N-hydroxysuccinimide ester (GMBS) from Sigma, 1-ethyl-3-(3-dimethylaminopropyl)carbodiimide hydrochloride (EDC) from Sigma and dimethyl suberimidate hydrochloride (DMS) from Sigma.
2) Other suitable non-amino acid linking regions are 1-ethyl-3-(3-dimethylaminopropyl) carbodiimide, N-ethyl-5-phenylisoaxolium-3-sulphonate, 1-cyclohexyl-3(2morpholinoethyl) carbodide metho-p-toluene sulphonate, N-ethoxycarbonyl-2-ethoxy 1,2, dihydroquinoline or glutaraldehyde.
3) Also suitable are the crosslinkers described in the 1999/2000 Pierce Products Catalogue from the Pierce Company, under the heading "Cross linking reagents: the SMPH, SMCC, LC-SMCC compounds, and preferably the Sulfo-KMUS compound.

Preferred chemical linking regions are PEG(NPC)2, (NH2) 2-PEG, t-BOC-NH-PEG-NH2, MAL-PEG-NHS, VS-PEG-NHS polymers from Shearwater and/or the Sulfo-KMUS compound from Pierce.

Detergent Components

The laundry detergent and/or fabric care compositions of the invention must contain at least one additional detergent and/or fabric care components. The precise nature of these additional components, and levels of incorporation thereof will depend on the physical form of the composition, and the nature of the cleaning operation for which it is to be used.

The laundry detergent and/or fabric care compositions of the present invention preferably further comprise a detergent ingredient selected from a surfactant selected from nonionic and/or anionic and/or cationic and/or mixtures thereof, another detergent enzyme, a bleaching agent, a dye transfer inhibiting polymer, a dispersant and/or a smectite clay.

The laundry detergent and/or fabric care compositions according to the invention can be liquid, paste, gels, bars, tablets, spray, foam, powder or granular forms. Granular compositions can also be in "compact" form, the liquid compositions can also be in a "concentrated" form.

The compositions of the invention may for example, be formulated as hand and machine laundry detergent compositions including laundry additive compositions and compositions suitable for use in the soaking and/or pretreatment of stained fabrics, rinse added fabric softener compositions. Pre- or post treatment of fabric include gel, spray and liquid fabric care compositions. A rinse cycle with or without the presence of softening agents is also contemplated.

When formulated as compositions suitable for use in a laundry machine washing method, the compositions of the invention preferably contain both a surfactant and a builder compound and additionally one or more detergent components preferably selected from organic polymeric compounds, bleaching agents, additional enzymes, suds suppressors, dispersants, lime-soap dispersants, soil suspension and anti-redeposition agents and corrosion inhibitors. Laundry compositions can also contain softening agents, as additional detergent components.

The compositions of the invention can also be used as detergent additive products in solid or liquid form. Such additive products are intended to supplement or boost the performance of conventional detergent compositions and can be added at any stage of the cleaning process.

If needed the density of the laundry detergent compositions herein ranges from 400 to 1200 g/liter, preferably 500 to 950 g/liter of composition measured at 20° C.

The "compact" form of the compositions herein is best reflected by density and, in terms of composition, by the amount of inorganic filler salt; inorganic filler salts are conventional ingredients of detergent compositions in powder form; in conventional detergent compositions, the filler salts are present in substantial amounts, typically 17–35% by weight of the total composition. In the compact compositions, the filler salt is present in amounts not exceeding 15% of the total composition, preferably not exceeding 10%, most preferably not exceeding 5% by weight of the composition. The inorganic filler salts, such as meant in the present compositions are selected from the alkali and alkaline-earth-metal salts of sulphates and chlorides. A preferred filler salt is sodium sulphate.

Liquid detergent compositions according to the present invention can also be in a "concentrated form", in such case, the liquid detergent compositions according the present invention will contain a lower amount of water, compared to conventional liquid detergents. Typically the water content of the concentrated liquid detergent is preferably less than 40%, more preferably less than 30%, most preferably less than 20% by weight of the detergent composition.

Surfactant System

Preferably, the laundry detergent and/or fabric care compositions according to the present invention further comprise a surfactant system wherein the surfactant can be selected from nonionic and/or anionic and/or cationic surfactants.

It has been surprisingly found that the combination of modified transferase with at least 5% of anionic surfactant, especially alkyl sulfate, alkyl ethoxy sulfates and linear alkylene sulfonate and/or at least 2% of nonionic surfactant of the alkyl ethoxylate type and/or cationic surfactant in the presence of anionic surfactant, provides refurbishes or restores improved tensile strength, enhanced anti-wrinkle, anti-shrinkage and anti-bobbling properties to fabrics, as well as provide better static control, fabric softness, colour appearance and fabric anti-wear properties and benefits. In addition, improved cleaning benefits are achieved with said combinations.

The surfactant is typically present at a level of from 0.1% to 60% by weight. More preferred levels of incorporation are 1% to 35% by weight, most preferably from 1% to 30% by weight of laundry detergent and/or fabric care compositions in accord with the invention.

The surfactant is preferably formulated to be compatible with enzyme components present in the composition. In liquid or gel compositions the surfactant is most preferably formulated such that it promotes, or at least does not degrade, the stability of any enzyme in these compositions.

Polyethylene, polypropylene, and polybutylene oxide condensates of alkyl phenols are suitable for use as the nonionic surfactant of the surfactant systems of the present invention, with the polyethylene oxide condensates being preferred. These compounds include the condensation products of alkyl phenols having an alkyl group containing from about 6 to about 14 carbon atoms, preferably from about 8 to about 14 carbon atoms, in either a straight-chain or branched-chain configuration with the alkylene oxide. In a preferred embodiment, the ethylene oxide is present in an amount equal to from about 2 to about 25 moles, more preferably from about 3 to about 15 moles, of ethylene oxide per mole of alkyl phenol. Commercially available nonionic surfactants of this type include Igepal™ CO-630, marketed by the GAF Corporation; and Triton™ X45, X-114, X-100 and X-102, all marketed by the Rohm & Haas Company. These surfactants are commonly referred to as alkylphenol alkoxylates (e.g., alkyl phenol ethoxylates).

The condensation products of primary and secondary aliphatic alcohols with from about 1 to about 25 moles of ethylene oxide are suitable for use as the nonionic surfactant of the nonionic surfactant systems of the present invention. The alkyl chain of the aliphatic alcohol can either be straight or branched, primary or secondary, and generally contains from about 8 to about 22 carbon atoms. Preferred are the condensation products of alcohols having an alkyl group containing from about 8 to about 20 carbon atoms, more preferably from about 10 to about 18 carbon atoms, with from about 2 to about 10 moles of ethylene oxide per mole of alcohol. About 2 to about 7 moles of ethylene oxide and most preferably from 2 to 5 moles of ethylene oxide per mole of alcohol are present in said condensation products. Examples of commercially available nonionic surfactants of this type include Tergitol™ 15-S-9 (the condensation product of $C_{11}$–$C_{15}$ linear alcohol with 9 moles ethylene oxide), Tergitol™ 24-L-6 NMW (the condensation product of $C_{12}$–$C_{14}$ primary alcohol with 6 moles ethylene oxide with a narrow molecular weight distribution), both marketed by Union Carbide Corporation; Neodol™ 45-9 (the condensation product of $C_{14}$–$C_{15}$ linear alcohol with 9 moles of ethylene oxide), Neodol™ 23-3 (the condensation product of $C_{12}$–$C_{13}$ linear alcohol with 3.0 moles of ethylene oxide), Neodol™ 45-7 (the condensation product of $C_{14}$–$C_{15}$ linear alcohol with 7 moles of ethylene oxide), Neodol™ 45-5 (the condensation product of $C_{14}$–$C_{15}$ linear alcohol with 5 moles of ethylene oxide) marketed by Shell Chemical Company, Kyro™ EOB (the condensation product of $C_{13}$–$C_{15}$ alcohol with 9 moles ethylene oxide), marketed by The Procter & Gamble Company, and Genapol LA O3O or O5O (the condensation product of $C_{12}$–$C_{14}$ alcohol with 3 or 5 moles of ethylene oxide) marketed by Hoechst. Preferred range of HLB in these products is from 8–11 and most preferred from 8–10.

Also useful as the nonionic surfactant of the surfactant systems of the present invention are the alkylpolysaccharides disclosed in U.S. Pat. No. 4,565,647, Llenado, issued Jan. 21, 1986, having a hydrophobic group containing from about 6 to about 30 carbon atoms, preferably from about 10 to about 16 carbon atoms and a polysaccharide, e.g. a polyglycoside, hydrophilic group containing from about 1.3 to about 10, preferably from about 1.3 to about 3, most preferably from about 1.3 to about 2.7 saccharide units. Any reducing saccharide containing 5 or 6 carbon atoms can be used, e.g., glucose, galactose and galactosyl moieties can be substituted for the glucosyl moieties (optionally the hydrophobic group is attached at the 2-, 3-, 4-, etc. positions thus giving a glucose or galactose as opposed to a glucoside or galactoside). The intersaccharide bonds can be, e.g., between the one position of the additional saccharide units and the 2-, 3-, 4-, and/or 6- positions on the preceding saccharide units. The preferred alkylpolyglycosides have the formula

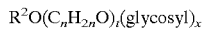

wherein $R^2$ is selected from the group consisting of alkyl, alkylphenyl, hydroxyalkyl, hydroxyalkylphenyl, and mixtures thereof in which the alkyl groups contain from about 10 to about 18, preferably from about 12 to about 14, carbon atoms; n is 2 or 3, preferably 2; t is from 0 to about 10, preferably 0; and x is from about 1.3 to about 10, preferably from about 1.3 to about 3, most preferably from about 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominately the 2-position.

The condensation products of ethylene oxide with a hydrophobic base formed by the condensation of propylene oxide with propylene glycol are also suitable for use as the additional nonionic surfactant systems of the present invention. The hydrophobic portion of these compounds will preferably have a molecular weight of from about 1500 to about 1800 and will exhibit water insolubility. The addition of polyoxyethylene moieties to this hydrophobic portion tends to increase the water solubility of the molecule as a whole, and the liquid character of the product is retained up to the point where the polyoxyethylene content is about 50% of the total weight of the condensation product, which corresponds to condensation with up to about 40 moles of ethylene oxide. Examples of compounds of this type include certain of the commercially-available Plurafac™ LF404 and Pluronic™ surfactants, marketed by BASF.

Also suitable for use as the nonionic surfactant of the nonionic surfactant system of the present invention, are the condensation products of ethylene oxide with the product resulting from the reaction of propylene oxide and ethylenediamine. The hydrophobic moiety of these products consists of the reaction product of ethylenediamine and excess propylene oxide, and generally has a molecular weight of from about 2500 to about 3000. This hydrophobic moiety is condensed with ethylene oxide to the extent that the condensation product contains from about 40% to about 80% by weight of polyoxyethylene and has a molecular weight of from about 5,000 to about 11,000. Examples of this type of nonionic surfactant include certain of the commercially available Tetronic™ compounds, marketed by BASF.

Preferred for use as the nonionic surfactant of the surfactant systems of the present invention are polyethylene oxide condensates of alkyl phenols, condensation products of primary and secondary aliphatic alcohols with from about 1 to about 25 moles of ethylene oxide, alkylpolysaccharides, and mixtures thereof. Most preferred are $C_8$–$C_{14}$ alkyl phenol ethoxylates having from 3 to 15 ethoxy groups and $C_8$–$C_{18}$ alcohol ethoxylates (preferably $C_{10}$ avg.) having from 2 to 10 ethoxy groups, and mixtures thereof.

Highly preferred nonionic surfactants are polyhydroxy fatty acid amide surfactants of the formula.

wherein $R^1$ is H, or $R^1$ is $C_{1-4}$ hydrocarbyl, 2-hydroxy ethyl, 2-hydroxy propyl or a mixture thereof, $R^2$ is $C_{5-31}$ hydrocarbyl, and Z is a polyhydroxyhydrocarbyl having a linear hydrocarbyl chain with at least 3 hydroxyls directly connected to the chain, or an alkoxylated derivative thereof. Preferably, $R^1$ is methyl, $R^2$ is a straight $C_{11-15}$ alkyl or $C_{16-18}$ alkyl or alkenyl chain such as coconut alkyl or mixtures thereof, and Z is derived from a reducing sugar such as glucose, fructose, maltose, lactose, in a reductive amination reaction.

Suitable anionic surfactants to be used are linear alkyl benzene sulfonate, alkyl ester sulfonate surfactants including linear esters of $C_8$–$C_{20}$ carboxylic acids (i.e., fatty acids) which are sulfonated with gaseous $SO_3$ according to The Journal of the American Oil Chemists Society", 52 (1975), pp. 323–329. Suitable starting materials would include natural fatty substances as derived from tallow, palm oil, etc. The preferred alkyl ester sulfonate surfactant, especially for laundry applications, comprise alkyl ester sulfonate surfactants of the structural formula:

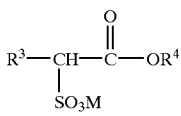

wherein $R^3$ is a $C_8$–$C_{20}$ hydrocarbyl, preferably an alkyl, or combination thereof, $R^4$ is a $C_1$–$C_6$ hydrocarbyl, preferably an alkyl, or combination thereof, and M is a cation which forms a water soluble salt with the alkyl ester sulfonate. Suitable salt-forming cations include metals such as sodium, potassium, and lithium, and substituted or unsubstituted ammonium cations, such as monoethanolamine, diethanolamine, and triethanolamine. Preferably, $R^3$ is $C_{10}$–$C_{16}$ alkyl, and $R^4$ is methyl, ethyl or isopropyl. Especially preferred are the methyl ester sulfonates wherein $R^3$ is $C_{10}$–$C_{16}$ alkyl.

Other suitable anionic surfactants include the alkyl sulfate surfactants which are water soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g. sodium, potassium, lithium), or ammonium or substituted ammonium (e.g. methyl-, dimethyl-, and trimethyl ammonium cations and quaternary ammonium cations such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12}$–$C_{16}$ are preferred for lower wash temperatures (e.g. below about 50° C.) and $C_{16-18}$ alkyl chains are preferred for higher wash temperatures (e.g. above about 50° C.).

Other anionic surfactants useful for detersive purposes can also be included in the laundry detergent and/or fabric care compositions of the present invention. These can include salts (including, for example, sodium, potassium, ammonium, and substituted ammonium salts such as mono-, di- and triethanolamine salts) of soap, $C_8$–$C_{22}$ primary of secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl glycerol sulfonates, fatty acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinates (especially saturated and unsaturated $C_{12}$–$C_{18}$ monoesters) and diesters of sulfosuccinates (especially saturated and unsaturated $C_6$–$C_{12}$ diesters), acyl sarcosinates, sulfates of alkylpolysaccharides such as the sulfates of alkylpolyglucoside (the nonionic nonsulfated compounds being described below), branched primary alkyl sulfates, and alkyl polyethoxy carboxylates such as those of the formula $RO(CH_2CH_2O)_k$—$CH_2COO$—M+ wherein R is a $C_8$–$C_{22}$ alkyl, k is an integer from 1 to 10, and M is a soluble salt-forming cation. Resin acids and hydrogenated resin acids are also suitable, such as rosin, hydrogenated rosin, and resin acids and hydrogenated resin acids present in or derived from tall oil.

Further examples are described in "Surface Active Agents and Detergents" (Vol. I and II by Schwartz, Perry and Berch). A variety of such surfactants are also generally disclosed in U.S. Pat. No. 3,929,678, issued Dec. 30, 1975 to Laughlin, et al. at Column 23, line 58 through Column 29, line 23 (herein incorporated by reference). When included therein, the laundry detergent compositions of the present invention typically comprise from about 1% to about 40%, preferably from about 3% to about 20% by weight of such anionic surfactants.

Highly preferred anionic surfactants include alkyl alkoxylated sulfate surfactants hereof are water soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl, trimethyl-ammonium cations and quaternary ammonium cations such as tetramethyl-ammonium and dimethyl piperdinium cations and those derived from alkylamines such as ethylamine, diethylamine, triethylamine, mixtures thereof, and the like. Exemplary surfactants are $C_{12}$–$C_{18}$ alkyl polyethoxylate (1.0) sulfate ($C_{12}$–$C_{18}E(1.0)M$), $C_{12}$–$C_{18}$ alkyl polyethoxylate (2.25) sulfate ($C_{12}$–$C_{18}E(2.25)M$), $C_{12}$–$C_{18}$ alkyl polyethoxylate (3.0) sulfate ($C_{12}$–$C_{18}E(3.0)M$), and $C_{12}$–$C_{18}$ alkyl polyethoxylate (4.0) sulfate ($C_{12}$–$C_{18}E(4.0)M$), wherein M is conveniently selected from sodium and potassium.

The laundry detergent and/or fabric care compositions of the present invention may also contain cationic, ampholytic, zwitterionic, and semi-polar surfactants, as well as the nonionic and/or anionic surfactants other than those already described herein.

Cationic detersive surfactants suitable for use in the laundry detergent and/or fabric care compositions of the present invention are those having one long-chain hydrocarbyl group. Examples of such cationic surfactants include the ammonium surfactants such as alkyltrimethylammonium halogenides, and those surfactants having the formula:

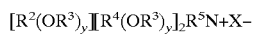

wherein $R^2$ is an alkyl or alkyl benzyl group having from about 8 to about 18 carbon atoms in the alkyl chain, each $R^3$ is selected from the group consisting of —$CH_2CH_2$—,—$CH_2CH(CH_3)$—, —$CH_2CH(CH_2OH)$—, —$CH_2CH_2CH_2$—, and mixtures thereof; each $R^4$ is selected from the group consisting of $C_1$–$C_4$ alkyl, $C_1$–$C_4$ hydroxyalkyl, benzyl ring structures formed by joining the two $R^4$ groups, —$CH_2CHOH$—$CHOHCOR^6CHOHCH_2OH$ wherein $R^6$ is any hexose or hexose polymer having a molecular weight less than about 1000, and hydrogen when y is not 0; $R^5$ is the same as $R^4$ or is an alkyl chain wherein the total number of carbon atoms of $R^2$ plus $R^5$ is not more than about 18; each y is from 0 to about 10 and the sum of the y values is from 0 to about 15; and X is any compatible anion.

Quaternary ammonium surfactant suitable for the present invention has the formula (I):

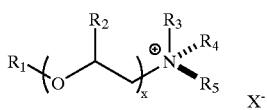

Formula I whereby R1 is a short chainlength alkyl (C6–C10) or alkylamidoalkyl of the formula (II):

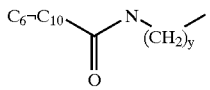

Formula II y is 2–4, preferably 3.
whereby R2 is H or a C1–C3 alkyl,
whereby x is 0–4, preferably 0–2, most preferably 0,
whereby R3, R4 and R5 are either the same or different and can be either a
short chain alkyl (C1–C3) or alkoxylated alkyl of the formula III,
whereby $X^-$ is a counterion, preferably a halide, e.g. chloride or methylsulfate.

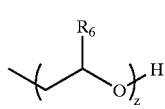

Formula III

R6 is $C_1$–$C_4$ and z is 1 or 2.
Preferred quat ammonium surfactants are those as defined in formula I whereby
$R_1$ is $C_8$, $C_{10}$ or mixtures thereof, x=o, $R_3$, $R_4$ =$CH_3$ and $R_5$ =$CH_2CH_2OH$.
Highly preferred cationic surfactants are the water-soluble quaternary ammonium compounds useful in the present composition having the formula:

$$R_1 R_2R_3R_4N^+X^- \quad (i)$$

wherein $R_1$ is $C_8$–$C_{16}$ alkyl, each of $R_2$, $R_3$ and $R_4$ is independently $C_1$–$C_4$ alkyl, $C_1$–$C_4$ hydroxy alkyl, benzyl, and —$(C_2H_{40})_xH$ where x has a value from 2 to 5, and X is an anion. Not more than one of $R_2$, $R_3$ or $R_4$ should be benzyl. The preferred alkyl chain length for $R_1$ is $C_{12}$–$C_{15}$ particularly where the alkyl group is a mixture of chain lengths derived from coconut or palm kernel fat or is derived synthetically by olefin build up or OXO alcohols synthesis. Preferred groups for $R_2R_3$ and $R_4$ are methyl and hydroxyethyl groups and the anion X may be selected from halide, methosulphate, acetate and phosphate ions. Examples of suitable quaternary ammonium compounds of formulae (i) for use herein are:
  coconut trimethyl ammonium chloride or bromide;
  coconut methyl dihydroxyethyl ammonium chloride or bromide;
  decyl triethyl ammonium chloride;
  decyl dimethyl hydroxyethyl ammonium chloride or bromide;
  $C_{12-15}$ dimethyl hydroxyethyl ammonium chloride or bromide;
  coconut dimethyl hydroxyethyl ammonium chloride or bromide;
  myristyl trimethyl ammonium methyl sulphate;
  lauryl dimethyl benzyl ammonium chloride or bromide;
  lauryl dimethyl (ethenoxy)$_4$ ammonium chloride or bromide;
  choline esters (compounds of formula (i) wherein $R_1$ is

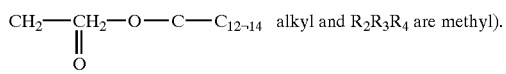 alkyl and $R_2R_3R_4$ are methyl).

di-alkyl imidazolines [compounds of formula (i)].

Other cationic surfactants useful herein are also described in U.S. Pat. No. 4,228,044, Cambre, issued Oct. 14, 1980 and in European Patent Application EP 000,224.

Typical cationic fabric softening components include the water-insoluble quaternary-ammonium fabric softening actives or thei corresponding amine precursor, the most commonly used having been di-long alkyl chain ammonium chloride or methyl sulfate.

Preferred cationic softeners among these include the following:

1) ditallow dimethylammonium chloride (DTDMAC);
2) dihydrogenated tallow dimethylammonium chloride;
3) dihydrogenated tallow dimethylammonium methylsulfate;
4) distearyl dimethylammonium chloride;
5) dioleyl dimethylammonium chloride;
6) dipalmityl hydroxyethyl methylammonium chloride;
7) stearyl benzyl dimethylammonium chloride;
8) tallow trimethylammonium chloride;
9) hydrogenated tallow trimethylammonium chloride;
10) $C_{12-14}$ alkyl hydroxyethyl dimethylammonium chloride;
11) $C_{12-18}$ alkyl dihydroxyethyl methylammonium chloride;
12) di(stearoyloxyethyl) dimethylammonium chloride (DSOEDMAC);
13) di(tallow-oxy-ethyl) dimethylammonium chloride;
14) ditallow imidazolinium methylsulfate;
15) 1-(2-tallowylamidoethyl)-2-tallowyl imidazolinium methylsulfate.

Biodegradable quaternary ammonium compounds have been presented as alternatives to the traditionally used di-long alkyl chain ammonium chlorides and methyl sulfates. Such quaternary ammonium compounds contain long chain alk(en)yl groups interrupted by functional groups such as carboxy groups. Said materials and fabric softening compositions containing them are disclosed in numerous publications such as EP-A-0,040,562, and EP-A-0,239,910.

The quaternary ammonium compounds and amine precursors herein have the formula (I) or (II), below:

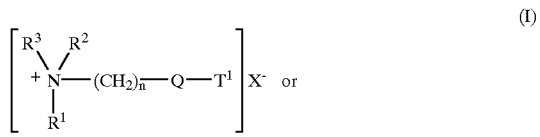

-continued

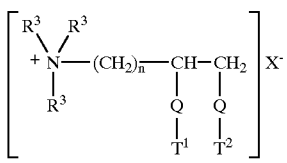
(II)

wherein

Q is selected from —O—C(O)—, —C(O)—O—, —O—C(O)—O—, —NR$^4$—C(O)—, —C(O)—NR$^4$—;

R$^1$ is (CH$_2$)$_n$-Q—T$^2$ or T$^3$;

R$^2$ is (CH$_2$)$_m$-Q—T$^4$ or T$^5$ or R$^3$;

R$^3$ is C$_1$–C$_4$ alkyl or C$_1$–C$_4$ hydroxyalkyl or H;

R$^4$ is H or C$_1$–C$_4$ alkyl or C$_1$–C$_4$ hydroxyalkyl;

T$^1$, T$^2$, T$^3$, T$^4$, T$^5$ are independently C$_{11}$–C$_{22}$ alkyl or alkenyl;

n and m are integers from 1 to 4; and

X$^-$ is a softener-compatible anion. Non-limiting examples of softener-compatible anions include chloride or methyl sulfate.

The alkyl, or alkenyl, chain T$^1$, T$^2$, T$^3$, T$^4$, T$^5$ must contain at least 11 carbon atoms, preferably at least 16 carbon atoms. The chain may be straight or branched. Tallow is a convenient and inexpensive source of long chain alkyl and alkenyl material. The compounds wherein T$^1$, T$^2$, T$^3$, T$^4$, T$^5$ represents the mixture of long chain materials typical for tallow are particularly preferred.

Specific examples of quaternary ammonium compounds suitable for use in the aqueous fabric softening compositions herein include:

1) N,N-di(tallowyl-oxy-ethyl)-N,N-dimethyl ammonium chloride;
2) N,N-di(tallowyl-oxy-ethyl)-N-methyl, N-(2-hydroxyethyl)ammonium methyl sulfate;
3) N,N-di(2-tallowyl-oxy-2-oxo-ethyl)-N,N-dimethyl ammonium chloride;
4) N,N-di(2-tallowyl-oxy-ethylcarbonyl-oxy-ethyl)-N,N-dimethyl ammonium chloride;
5) N-(2-tallowyl-oxy-2-ethyl)-N-(2-tallowyl-oxy-2-oxo-ethyl)-N,N-dimethyl ammonium chloride;
6) N,N,N-tri(tallowyl-oxy-ethyl)-N-methyl ammonium chloride;
7) N-(2-tallowyl-oxy-2-oxo-ethyl)-N-(tallowyl-N,N-dimethyl-ammonium chloride; and
8) 1,2-ditallowyl-oxy-3-trimethylammoniopropane chloride;

and mixtures of any of the above materials.

When included therein, the laundry detergent and/or fabric care compositions of the present invention typically comprise from 0.2% to about 25%, preferably from about 1% to about 8% by weight of such cationic surfactants.

Conventional Detergent Enzymes

The laundry detergent and/or fabric care compositions can in addition to the modified transferase enzyme, further comprise one or more enzymes which provide cleaning performance, fabric care and/or sanitisation benefits.

It has also been surprisingly found that the combination of a modified transferase with a detergent enzyme—especially a protease, cellulase, lipase and/or amylase—provides, refurbishes or restores improved tensile strength, enhanced anti-wrinkle, anti-shrinkage, anti-bobbling properties to fabrics, as well as provide better static control, fabric softness, colour appearance and fabric anti-wear properties and benefits. In addition, improved cleaning benefits are achieved with said combinations.

Said enzymes include enzymes selected from cellulases, hemicellulases, peroxidases, proteases, gluco-amylases, amylases, xylanases, lipases, phospholipases, esterases, cutinases, pectinases, keratanases, reductases, oxidases, phenoloxidases, lipoxygenases, ligninases, pullulanases, tannases, pentosanases, malanases, β-glucanases, arabinosidases, hyaluronidase, chondroitinase, laccase or mixtures thereof.

A preferred combination is a laundry detergent and/or fabric care composition having cocktail of conventional applicable enzymes like protease, amylase, lipase, cutinase and/or cellulase in conjunction with one or more plant cell wall degrading enzymes.

The cellulases usable in the present invention include both bacterial or fungal cellulases. Preferably, they will have a pH optimum of between 5 and 12 and a specific activity above 50 CEVU/mg (Cellulose Viscosity Unit). Suitable cellulases are disclosed in U.S. Pat. No. 4,435,307, Barbesgoard et al, J61078384 and WO96/02653 which discloses fungal cellulase produced respectively from *Humicola insolens, Trichoderma, Thielavia* and *Sporotrichum*. EP 739 982 describes cellulases isolated from novel Bacillus species. Suitable cellulases are also disclosed in GB-A-2.075.028; GB-A-2.095.275; DE-OS-2.247.832 and WO95/126398. Examples of such cellulases are cellulases produced by a strain of *Humicola insolens* (*Humicola grisea* var. *thermoidea*), particularly the Humicola strain DSM 1800.

Other suitable cellulases are cellulases originated from *Humicola insolens* having a molecular weight of about 50 KDa, an isoelectric point of 5.5 and containing 415 amino acids; and a ~43 kD endoglucanase derived from *Humicola insolens*, DSM 1800, exhibiting cellulase activity; a preferred endoglucanase component has the amino acid sequence disclosed in PCT Patent Application No. WO 91/17243. Also suitable cellulases are the EGIII cellulases from *Trichoderma longibrachiatum* described in WO94/21801, Genencor, published Sep. 29, 1994. Especially suitable cellulases are the cellulases having color care benefits. Examples of such cellulases are cellulases described in European patent application No. 91202879.2, filed Nov. 6, 1991 (Novo). Carezyme and Celluzyme (Novo Nordisk A/S) are especially useful. See also WO91/17244 and WO91/21801. Other suitable cellulases for fabric care and/or cleaning properties are described in WO96/34092, WO96/17994 and WO95/24471. Said cellulases are normally incorporated in the laundry detergent and/or fabric care composition at levels from 0.0001% to 2% of pure enzyme by weight of the laundry detergent and/or fabric care composition.

Peroxidase enzymes are used in combination with oxygen sources, e.g. percarbonate, perborate, persulfate, hydrogen peroxide, etc and with a phenolic substrate as bleach enhancing molecule. They are used for "solution bleaching", i.e. to prevent transfer of dyes or pigments removed from substrates during wash operations to other substrates in the wash solution. Peroxidase enzymes are known in the art, and include, for example, horseradish peroxidase, ligninase and haloperoxidase such as chloro- and bromo-peroxidase. Peroxidase-containing detergent compositions are disclosed, for example, in PCT International Application WO 89/099813, WO89/09813 and in European Patent application EP No. 91202882.6, filed on Nov. 6, 1991 and EP No. 96870013.8, filed Feb. 20, 1996. Also suitable is the laccase enzyme. Enhancers are generally comprised at a level of from 0.1% to 5% by weight of total composition. Preferred enhancers are substituted phenthiazine and phenoxasine 10-Phenothiazinepropionicacid (PPT), 10-ethylphenothiazine-4-carboxylic acid (EPC), 10-phenoxazinepropionic acid (POP) and 10-methylphenoxazine (described in WO 94/12621) and substituted syringates (C3–C5 substituted alkyl syringates) and phenols. Sodium percarbonate or perborate are preferred sources of hydrogen peroxide. Said peroxidases are normally incorporated in the laundry detergent and/or fabric care composition at levels from 0.0001% to 2% of pure enzyme by weight of the laundry detergent and/or fabric care composition.

Other preferred enzymes that can be included in the laundry detergent and/or fabric care compositions of the present invention include lipases. Suitable lipase enzymes for detergent usage include those produced by microorganisms of the Pseudomonas group, such as Pseudomonas stutzeri ATCC 19.154, as disclosed in British Patent 1,372,034. Suitable lipases include those which show a positive immunological cross-reaction with the antibody of the lipase, produced by the microorganism Pseudomonas fluorescent IAM 1057. This lipase is available from Amano Pharmaceutical Co. Ltd., Nagoya, Japan, under the trade name Lipase P "Amano," hereinafter referred to as "Amano-P". Other suitable commercial lipases include Amano-CES, lipases ex *Chromobacter viscosum*, e.g. *Chromobacter viscosum* var. *lipolyticum* NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. Especially suitable lipases are lipases such as M1 Lipase$^R$ and Lipomax$^R$ (Gist-Brocades) and Lipolase$^R$ and Lipolase Ultra$^R$(Novo) which have found to be very effective when used in combination with the compositions of the present invention. Also suitables are the lipolytic enzymes described in EP 258 068, WO 92/05249 and WO 95/22615 by Novo Nordisk and in WO 94/03578, WO 95/35381 and WO 96/00292 by Unilever. Also suitable are cutinases [EC 3.1.1.50] which can be considered as a special kind of lipase, namely lipases which do not require interfacial activation. Addition of cutinases to detergent compositions have been described in e.g. WO-A-88/09367 (Genencor); WO 90/09446 (Plant Genetic System) and WO 94/14963 and WO 94/14964 (Unilever). The lipases and/or cutinases are normally incorporated in the laundry detergent and/or fabric care composition at levels from 0.0001% to 2% of pure enzyme by weight of the laundry detergent and/or fabric care composition.

Suitable proteases are the subtilisins which are obtained from particular strains of *B. subtilis* and *B. licheniformis* (subtilisin BPN and BPN'). One suitable protease is obtained from a strain of Bacillus, having maximum activity throughout the pH range of 8–12, developed and sold as ESPERASE® by Novo Industries A/S of Denmark, hereinafter "Novo". The preparation of this enzyme and analogous enzymes is described in GB 1,243,784 to Novo. Other suitable proteases include ALCALASE®, DURAZYM® and SAVINASE® from Novo and MAXATASE®, MAXACAL®, PROPERASE® and MAXAPEM® (protein engineered Maxacal) from Gist-Brocades. Proteolytic enzymes also encompass modified bacterial serine proteases, such as those described in European Patent Application Serial Number 87 303761.8, filed Apr. 28, 1987 (particularly pages 17, 24 and 98), and which is called herein "Protease B", and in European Patent Application 199,404, Venegas, published Oct. 29, 1986, which refers to a modified bacterial serine protealytic enzyme which is called "Protease A" herein. Suitable is the protease called herein "Protease C", which is a variant of an alkaline serine protease from Bacillus in which lysine replaced arginine at position 27, tyrosine replaced valine at position 104, serine replaced asparagine at position 123, and alanine replaced threonine at position 274. Protease C is described in EP 90915958:4, corresponding to WO 91/06637, Published May 16, 1991. Genetically modified variants, particularly of Protease C, are also included herein.

A preferred protease referred to as "Protease D" is a carbonyl hydrolase variant having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135 +156, +166, +195 +197, +204, +206, +210, +216, +217, +218, +222, +260, +265, and/or +274 according to the numbering of *Bacillus amyloliquefaciens subtilisin*, as described in WO95/10591 and in the patent application of C. Ghosh, et al, "Bleaching Compositions Comprising Protease Enzymes" having U.S. Ser. No. 08/322,677, filed Oct. 13, 1994. Also suitable is a carbonyl hydrolase variant of the protease described in WO95/10591, having an amino acid sequence derived by replacement of a plurality of amino acid residues replaced in the precursor enzyme corresponding to position +210 in combination with one or more of the following residues: +33, +62, +67, +76, +100, +101, +103, +104, +107, +128, +129, +130, +132, +135, +156, +158, +164, +166, +167, +170, +209, +215, +217, +218, and +222, where the numbered position corresponds to naturally-occurring subtilisin from *Bacillus amyloliquefaciens* or to equivalent amino acid residues in other carbonyl hydrolases or subtilisins, such as *Bacillus lentus subtilisin* (co-pending patent application U.S. Ser. No. 60/048,550, filed Jun. 04, 1997).

Also preferred proteases are multiply-substituted protease variants. These protease variants comprise a substitution of an amino acid residue with another naturally occurring amino acid residue at an amino acid residue position corresponding to position 103 of *Bacillus amyloliquefaciens subtilisin* in combination with a substitution of an amino acid residue positions corresponding to positions 1, 3, 4, 8, 9, 10, 12, 13, 16, 17, 18, 19, 20, 21, 22, 24, 27, 33, 37, 38, 42, 43, 48, 55, 57, 58, 61, 62, 68, 72, 75, 76, 77, 78, 79, 86, 87, 89, 97, 98, 99, 101, 102, 104, 106, 107, 109, 111, 114, 116, 117, 119, 121, 123, 126, 128, 130, 131, 133, 134, 137, 140, 141, 142, 146, 147, 158, 159, 160, 166, 167, 170, 173, 174, 177, 181, 182, 183, 184, 185, 188, 192, 194, 198, 203, 204, 205, 206, 209, 210, 211, 212, 213, 214, 215, 216, 217, 218, 222, 224, 227, 228, 230, 232, 236, 237, 238, 240, 242, 243, 244, 245, 246, 247, 248, 249, 251, 252, 253, 254, 255, 256, 257, 258, 259, 260, 261, 262, 263, 265, 268, 269, 270, 271, 272, 274 and 275 of *Bacillus amyloliquefaciens subtilisin*; wherein when said protease variant includes a substitution of amino acid residues at positions corresponding to positions 103 and 76, there is also a substitution of an amino acid residue at one or more amino acid residue positions other than amino acid residue positions corresponding to positions 27, 99, 101, 104, 107, 109, 123, 128, 166, 204, 206, 210, 216, 217, 218, 222, 260, 265 or 274 of *Bacillus amyloliquefaciens subtilisin* and/or multiply-substituted protease variants comprising a substitution of an amino acid residue with another naturally occurring amino acid residue at one or more amino acid residue positions corresponding to positions 62, 212, 230, 232, 252 and 257 of *Bacillus amyloliquefaciens subtilisin* as described in PCT application Nos. PCT/US98/22588, PCT/US98/22482 and PCT/US98/22486 all filed on Oct. 23, 1998 from The Procter & Gamble Company. Also suitable for the present invention are proteases described in patent applications EP 251 446 and WO 91/06637, protease BLAP® described in WO91102792 and their variants described in WO 95/23221. See also a high pH protease from Bacillus sp. NCIMB 40338 described in WO 93/18140 A to Novo. Enzymatic detergents comprising protease, one or more other enzymes, and a reversible protease inhibitor are described in WO 92/03529 A to Novo. When desired, a protease having decreased adsorption and increased hydrolysis is available as described in WO 95/07791 to Procter & Gamble. A recombinant trypsin-like protease for detergents suitable herein is described in WO 94/25583 to Novo. Other suitable proteases are described in EP 516 200 by Unilever. The proteolytic enzymes are incorporated in the laundry detergent and/or fabric care compositions of the present invention a level of from 0.0001% to 2%, preferably from 0.001% to 0.2%, more preferably from 0.005% to 0.1% pure enzyme by weight of the composition.

Amylases ($\alpha$ and/or $\beta$) can be included for removal of carbohydrate-based stains. WO94/02597, Novo Nordisk A/S published Feb. 03, 1994, describes cleaning compositions which incorporate mutant amylases. See also WO95/10603, Novo Nordisk A/S, published Apr. 20, 1995. Other amylases known for use in cleaning compositions include both $\alpha$- and $\beta$amylases. $\alpha$-Amylases are known in the art and include those disclosed in U.S. Pat. No. 5,003,257; EP 252,666; WO/91/00353; FR 2,676,456; EP 285,123; EP 525,610; EP 368,341; and British Patent specification no. 1,296,839 (Novo). Other suitable amylases are stability-enhanced amylases described in WO94/18314, published Aug. 18, 1994 and WO96/05295, Genencor, published Feb. 22, 1996 and amylase variants having additional modification in the immediate parent available from Novo Nordisk A/S, disclosed in WO 95/10603, published April 1995. Also suitable are amylases described in EP 277 216, WO95/26397 and WO96/23873 (all by Novo Nordisk). Examples of commercial $\alpha$-amylases products are Purafect Ox Am® from Genencor and Termamyl®, Ban®,Fungamyl® and Duramyl®, all available from Novo Nordisk A/S Denmark. WO95/26397 describes other suitable amylases: $\alpha$-amylases characterised by having a specific activity at least 25% higher than the specific activity of Termamyl® at a temperature range of 25° C. to 55° C. and at a pH value in the range of 8 to 10, measured by the Phadebas® $\alpha$-amylase activity assay. Suitable are variants of the above enzymes, described in WO96/23873 (Novo Nordisk). Other amylolytic enzymes with improved properties with respect to the activity level and the combination of thermostability and a higher activity level are described in WO95/35382. The amylolytic enzymes are incorporated in the laundry detergent and/or fabric care compositions of the present invention a level of from 0.0001% to 2%, preferably from 0.00018% to 0.06%, more preferably from 0.00024% to 0.048% pure enzyme by weight of the composition.

The above-mentioned enzymes may be of any suitable origin, such as vegetable, animal, bacterial, fungal and yeast origin. Origin can further be mesophilic or extremophilic (psychrophilic, psychrotrophic, thermophilic, barophilic, alkalophilic, acidophilic, halophilic, etc.). Purified or non-purified forms of these enzymes may be used. Nowadays, it is common practice to modify wild-type enzymes via protein/genetic engineering techniques in order to optimise their performance efficiency in the cleaning compositions of the invention. For example, the variants may be designed such that the compatibility of the enzyme to commonly encountered ingredients of such compositions is increased. Alternatively, the variant may be designed such that the optimal pH, bleach or chelant stability, catalytic activity and the like, of the enzyme variant is tailored to suit the particular cleaning application.

In particular, attention should be focused on amino acids sensitive to oxidation in the case of bleach stability and on surface charges for the surfactant compatibility. The isoelectric point of such enzymes may be modified by the substitution of some charged amino acids, e.g. an increase in isoelectric point may help to improve compatibility with anionic surfactants. The stability of the enzymes may be further enhanced by the creation of e.g. additional salt bridges and enforcing calcium binding sites to increase chelant stability. Special attention must be paid to the cellulases as most of the cellulases have separate binding domains (CBD). Properties of such enzymes can be altered by modifications in these domains.

Said enzymes are normally incorporated in the laundry detergent and/or fabric care composition at levels from 0.0001% to 2% of pure enzyme by weight of the laundry detergent and/or fabric care composition. The enzymes can be added as separate single ingredients (prills, granulates, stabilized liquids, etc . . . containing one enzyme ) or as mixtures of two or more enzymes ( e.g. cogranulates).

Other suitable detergent ingredients that can be added are enzyme oxidation scavengers which are described in Copending European Patent application 92870018.6 filed on Jan. 31, 1992. Examples of such enzyme oxidation scavengers are ethoxylated tetraethylene polyamines.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilised by various techniques. Enzyme stabilisation techniques are disclosed and exemplified in U.S. Pat. No. 3,600,319, Aug. 17, 1971, Gedge et al, EP 199,405 and EP 200,586, Oct. 29, 1986, Venegas. Enzyme stabilisation systems are also described, for example, in U.S. Pat. No. 3,519,570. A useful Bacillus, sp. AC13 giving proteases, xylanases and cellulases, is described in WO 9401532 A to Novo.

Bleaching Agent

The laundry detergent and/or fabric care compositions of the present invention can comprise in addition to the modified transferase, a bleaching agent.

It has also been surprisingly found that the combination of a modified transferase with a bleaching agent achieved improved whiteness, provides, refurbishes or restores improved tensile strength, enhanced anti-wrinkle, anti-shrinkage, anti-bobbling properties to fabrics, as well as provide better static control, fabric softness, colour appearance and fabric anti-wear properties and benefits, especially enhances the fabric feel properties. In addition, improved cleaning benefits are achieved with said combination.

Bleaching agents include as hydrogen peroxide, PB1, PB4 and percarbonate with a particle size of 400–800 microns. These bleaching agent components can include one or more oxygen bleaching agents and, depending upon the bleaching agent chosen, one or more bleach activators. When present oxygen bleaching compounds will typically be present at levels of from about 1% to about 25%.

The bleaching agent component for use herein can be any of the bleaching agents useful for cleaning compositions including oxygen bleaches as well as others known in the art. The bleaching agent suitable for the present invention can be an activated or non-activated bleaching agent.

One category of oxygen bleaching agent that can be used encompasses percarboxylic acid bleaching agents and salts thereof. Suitable examples of this class of agents include magnesium monoperoxyphthalate hexahydrate, the magnesium salt of meta-chloro perbenzoic acid, 4-nonylamino-4-oxoperoxybutyric acid and diperoxydodecanedioic acid. Such bleaching agents are disclosed in U.S. Pat. No. 4,483,781, U.S. patent application Ser. No. 740,446, European Patent Application 0,133,354 and U.S. Pat. No. 4,412,934. Highly preferred bleaching agents also include 6-nonylamino-6-oxoperoxycaproic acid as described in U.S. Pat. No. 4,634,551. Another category of bleaching agents that can be used encompasses the halogen bleaching agents. Examples of hypohalite bleaching agents, for example, include trichloro isocyanuric acid and the sodium and potassium dichloroisocyanurates and N-chloro and N-bromo alkane sulphonamides. Such materials are normally added at 0.5–10% by weight of the finished product, preferably 1–5% by weight.

The hydrogen peroxide releasing agents can be used in combination with bleach activators such as tetraacetylethylenediamine (TAED), nonanoyloxybenzene-sulfonate (NOBS, described in U.S. Pat. No. 4,412,934), 3,5,-trimethylhexanoloxybenzenesulfonate (ISONOBS, described in EP 120,591) or pentaacetylglucose (PAG)or Phenolsulfonate ester of N-nonanoyl-6-aminocaproic acid (NACA-OBS, described in WO94/28106), which are perhydrolyzed to form a peracid as the active bleaching species, leading to improved bleaching effect. Also suitable activators are acylated citrate esters such as disclosed in Copending European Patent Application No. 91870207.7.

Useful bleaching agents, including peroxyacids and bleaching systems comprising bleach activators and peroxygen bleaching compounds for use in laundry detergent and/or fabric care compositions according to the invention are described in our co-pending applications U.S. Ser. No. 08/136,626, PCT/US95/07823, WO95/27772, WO95/27773, WO95/27774 and WO95/27775.

The hydrogen peroxide may also be present by adding an enzymatic system (i.e. an enzyme and a substrate therefore) which is capable of generating hydrogen peroxide at the beginning or during the washing and/or rinsing process. Such enzymatic systems are disclosed in EP Patent Application 91202655.6 filed Oct. 9, 1991.

Metal-containing catalysts for use in bleach compositions, include cobalt-containing catalysts such as Pentaamine acetate cobalt(III) salts and manganese-containing catalysts such as those described in EPA 549 271; EPA 549 272; EPA 458 397; U.S. Pat. No. 5,246,621; EPA 458 398; U.S. Pat. No. 5,194,416 and U.S. Pat. No. 5,114,611. Bleaching composition comprising a peroxy compound, a manganese-containing bleach catalyst and a chelating agent is described in the patent application No 94870206.3.

Bleaching agents other than oxygen bleaching agents are also known in the art and can be utilized herein. One type of non-oxygen bleaching agent of particular interest includes photoactivated bleaching agents such as the sulfonated zinc and/or aluminum phthalocyanines. These materials can be deposited upon the substrate during the washing process. Upon irradiation with light, in the presence of oxygen, such as by hanging clothes out to dry in the daylight, the sulfonated zinc phthalocyanine is activated and, consequently, the substrate is bleached. Preferred zinc phthalocyanine and a photoactivated bleaching process are described in U.S. Pat. No. 4,033,718. Typically, laundry detergent and/or fabric care compositions will contain about 0.025% to about 1.25%, by weight, of sulfonated zinc phthalocyanine.

Dye Transfer Inhibition

The laundry detergent and/or fabric care compositions of the present invention preferably further include compounds for inhibiting dye transfer from one fabric to another of solubilised and suspended dyes encountered during fabric laundering operations involving coloured fabrics.

It has also been surprisingly found that the combination of a modified transferase with a dye transfer inhibiting agent provides, refurbishes or restores improved tensile strength, enhanced anti-wrinkle, anti-shrinkage, anti-bobbling properties to fabrics, as well as provide better static control, fabric softness, colour appearance and fabric anti-wear properties and benefits. In addition, improved cleaning benefits are achieved with said combination.

Polymeric Dye Transfer Inhibiting Agents

The laundry detergent and/or fabric care compositions according to the present invention may also comprise from 0.001% to 10%, preferably from 0.01% to 2%, more preferably from 0.05% to 1% by weight of polymeric dye transfer inhibiting agents. Said polymeric dye transfer inhibiting agents are normally incorporated into laundry detergent and/or fabric care compositions in order to inhibit the transfer of dyes from colored fabrics onto fabrics washed therewith. These polymers have the ability to complex or adsorb the fugitive dyes washed out of dyed fabrics before the dyes have the opportunity to become attached to other articles in the wash. Especially suitable polymeric dye transfer inhibiting agents are polyamine N-oxide polymers, copolymers of N-vinylpyrrolidone and N-vinylimidazole, polyvinylpyrrolidone polymers, polyvinyloxazolidones and polyvinylimidazoles or mixtures thereof. Addition of such polymers also enhances the performance of the enzymes according the invention.

a) Polyamine N-oxide polymers

The polyamine N-oxide polymers suitable for use contain units having the following structure formula:

(I)

wherein P is a polymerisable unit, whereto the R—N—O group can be attached to or wherein the R—N—O group forms part of the polymerisable unit or a combination of both.

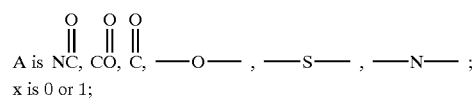

x is 0 or 1;

R are aliphatic, ethoxylated aliphatics, aromatic, heterocyclic or alicyclic groups or any combination thereof whereto the nitrogen of the N—O group can be attached or wherein the nitrogen of the N—O group is part of these groups.

The N—O group can be represented by the following general structures:

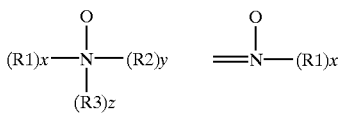

wherein R1, R2, and R3 are aliphatic groups, aromatic, heterocyclic or alicyclic groups or combinations thereof, x or/and y or/and z is 0 or 1 and wherein the nitrogen of the N—O group can be attached or wherein the nitrogen of the N—O group forms part of these groups.

The N—O group can be part of the polymerisable unit (P) or can be attached to the polymeric backbone or a combination of both. Suitable polyamine N-oxides wherein the N—O group forms part of the polymerisable unit comprise polyamine N-oxides wherein R is selected from aliphatic, aromatic, alicyclic or heterocyclic groups. One class of said polyamine N-oxides comprises the group of polyamine N-oxides wherein the nitrogen of the N—O group forms part of the R-group. Preferred polyamine N-oxides are those wherein R is a heterocyclic group such as pyrridine, pyrrole, imidazole, pyrrolidine, piperidine, quinoline, acridine and derivatives thereof. Another class of said polyamine N-oxides comprises the group of polyamine N-oxides wherein the nitrogen of the N—O group is attached to the R-group.

Other suitable polyamine N-oxides are the polyamine oxides whereto the N—O group is attached to the polymerisable unit. Preferred class of these polyamine N-oxides are the polyamine N-oxides having the general formula (I) wherein R is an aromatic, heterocyclic or alicyclic groups wherein the nitrogen of the N—O functional group is part of said R group. Examples of these classes are polyamine oxides wherein R is a heterocyclic compound such as pyrridine, pyrrole, imidazole and derivatives thereof. Another preferred class of polyamine N-oxides are the polyamine oxides having the general formula (I) wherein R are aromatic, heterocyclic or alicyclic groups wherein the nitrogen of the N—O functional group is attached to said R groups. Examples of these classes are polyamine oxides wherein R groups can be aromatic such as phenyl.

Any polymer backbone can be used as long as the amine oxide polymer formed is water-soluble and has dye transfer inhibiting properties. Examples of suitable polymeric backbones are polyvinyls, polyalkylenes, polyesters, polyethers, polyamide, polyimides, polyacrylates and mixtures thereof.

The amine N-oxide polymers of the present invention typically have a ratio of amine to the amine N-oxide of 10:1 to 1:1000000. However the amount of amine oxide groups present in the polyamine oxide polymer can be varied by appropriate copolymerization or by appropriate degree of N-oxidation. Preferably, the ratio of amine to amine N-oxide is from 2:3 to 1:1000000. More preferably from 1:4 to 1:1000000, most preferably from 1:7 to 1:1000000. The polymers of the present invention actually encompass random or block copolymers where one monomer type is an amine N-oxide and the other monomer type is either an amine N-oxide or not. The amine oxide unit of the polyamine N-oxides has a PKa<10, preferably PKa<7, more preferred PKa<6. The polyamine oxides can be obtained in almost any degree of polymerisation. The degree of polymerisation is not critical provided the material has the desired water-solubility and dye-suspending power.

Typically, the average molecular weight is within the range of 500 to 1000,000; preferably from 1,000 to 50,000, more preferably from 2,000 to 30,000, most preferably from 3,000 to 20,000.

b) Copolymers of N-vinylpyrrolidone and N-vinylimidazole

The N-vinylimidazole N-vinylpyrrolidone polymers used in the present invention have an average molecular weight range from 5,000–1,000,000, preferably from 5,000–200,000. Highly preferred polymers for use in laundry detergent and/or fabric care compositions according to the present invention comprise a polymer selected from N-vinylimidazole N-vinylpyrrolidone copolymers wherein said polymer has an average molecular weight range from 5,000 to 50,000 more preferably from 8,000 to 30,000, most preferably from 10,000 to 20,000. The average molecular weight range was determined by light scattering as described in Barth H. G. and Mays J. W. Chemical Analysis Vol 113,"Modern Methods of Polymer Characterization". Highly preferred N-vinylimidazole N-vinylpyrrolidone copolymers have an average molecular weight range from 5,000 to 50,000; more preferably from 8,000 to 30,000; most preferably from 10,000 to 20,000.

The N-vinylimidazole N-vinylpyrrolidone copolymers characterized by having said average molecular weight range provide excellent dye transfer inhibiting properties while not adversely affecting the cleaning performance of laundry detergent and/or fabric care compositions formulated therewith. The N-vinylimidazole N-vinylpyrrolidone copolymer of the present invention has a molar ratio of N-vinylimidazole to N-vinylpyrrolidone from 1 to 0.2, more preferably from 0.8 to 0.3, most preferably from 0.6 to 0.4.

c) Polyvinylpyrrolidone

The laundry detergent and/or fabric care compositions of the present invention may also utilize polyvinylpyrrolidone ("PVP") having an average molecular weight of from about 2,500 to about 400,000, preferably from about 5,000 to about 200,000, more preferably from about 5,000 to about 50,000, and most preferably from about 5,000 to about 15,000. Suitable polyvinylpyrrolidones are commercially vailable from ISP Corporation, New York, N.Y. and Montreal, Canada under the product names PVP K-15 (viscosity molecular weight of 10,000), PVP K-30 (average molecular weight of 40,000), PVP K-60 (average molecular weight of 160,000), and PVP K-90 (average molecular weight of 360,000). Other suitable polyvinylpyrrolidones which are commercially available from BASF Cooperation include Sokalan HP 165 and Sokalan HP 12; polyvinylpyrrolidones known to persons skilled in the detergent field (see for example EP-A-262,897 and EP-A-256,696).

d) Polyvinyloxazolidone

The laundry detergent and/or fabric care compositions of the present invention may also utilize polyvinyloxazolidone as a polymeric dye transfer inhibiting agent. Said polyvinyloxazolidones have an average molecular weight of from about 2,500 to about 400,000, preferably from about 5,000 to about 200,000, more preferably from about 5,000 to about 50,000, and most preferably from about 5,000 to about 15,000.

e) Polyvinylimidazole

The laundry detergent and/or fabric care compositions of the present invention may also utilize polyvinylimidazole as polymeric dye transfer inhibiting agent. Said polyvinylimidazoles have an average about 2,500 to about 400,000, preferably from about 5,000 to about 200,000, more preferably from about 5,000 to about 50,000, and most preferably from about 5,000 to about 15,000.

f) Cross-linked Polymers

Cross-linked polymers are polymers whose backbone are interconnected to a certain degree; these links can be of chemical or physical nature, possibly with active groups n the backbone or on branches; cross-linked polymers have been described in the Journal of Polymer Science, volume 22, pages 1035–1039. In one embodiment, the cross-linked polymers are made in such a way that they form a three-dimensional rigid structure, which can entrap dyes in the pores formed by the three-dimensional structure. In another embodiment, the cross-linked polymers entrap the dyes by swelling. Such cross-linked polymers are described in the co-pending patent application 94870213.9

Dispersants

The laundry detergent and/or fabric care composition of the present invention can also further comprise dispersants. It has also been surprisingly found that the combination of a modified transferase with a dispersant provides, refurbishes or restores improved tensile strength, enhanced anti-wrinkle, anti-shrinkage, anti-bobbling properties to fabrics, as well as provide better static control, fabric softness, colour appearance and fabric anti-wear properties and benefits. In addition, improved cleaning benefits are achieved with said combination.

Suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 1,000 to 100,000. Especially, copolymer of acrylate and methylacrylate such as the 480N having a molecular weight of 4000, at a level from 0.5–20% by weight of composition can be added in the laundry detergent and/or fabric care compositions of the present invention.

The compositions of the invention may contain a lime soap peptiser compound, which has preferably a lime soap dispersing power (LSDP), as defined hereinafter of no more than 8, preferably no more than 7, most preferably no more than 6. The lime soap peptiser compound is preferably present at a level from 0% to 20% by weight. A numerical measure of the effectiveness of a lime soap peptiser is given by the lime soap dispersant power (LSDP) which is determined using the lime soap dispersant test as described in an article by H. C. Borghetty and C. A. Bergman, J. Am. Oil. Chem. Soc., volume 27, pages 88–90, (1950). This lime soap dispersion test method is widely used by practitioners in this art field being referred to, for example, in the following review articles; W. N. Linfield, Surfactant science Series, Volume 7, page 3; W. N. Linfield, Tenside surf. det., volume 27, pages 159–163, (1990); and M. K. Nagarajan, W. F. Masler, Cosmetics and Toiletries, volume 104, pages 71–73, (1989). The LSDP is the % weight ratio of dispersing agent to sodium oleate required to disperse the lime soap deposits formed by 0.025 g of sodium oleate in 30 ml of water of 333 ppm $CaCo_3$ (Ca:Mg=3:2) equivalent hardness.

Surfactants having good lime soap peptiser capability will include certain amine oxides, betaines, sulfobetaines, alkyl ethoxysulfates and ethoxylated alcohols. Exemplary surfactants having a LSDP of no more than 8 for use in accord with the present invention include $C_{16}$–$C_{18}$ dimethyl amine oxide, $C_{12}$–$C_{18}$ alkyl ethoxysulfates with an average degree of ethoxylation of from 1–5, particularly $C_{12}$–$C_{15}$ alkyl ethoxysulfate surfactant with a degree of ethoxylation of amount 3 (LSDP=4), and the $C_{14}$–$C_{15}$ ethoxylated alcohols with an average degree of ethoxylation of either 12 (LSDP= 6) or 30, sold under the tradenames Lutensol A012 and Lutensol A030 respectively, by BASF GmbH.

Polymeric lime soap peptisers suitable for use herein are described in the article by M. K. Nagarajan, W. F. Masler, to be found in Cosmetics and Toiletries, volume 104, pages 71–73, (1989).

Hydrophobic bleaches such as 4-[N-octanoyl-6-aminohexanoyl]benzene sulfonate, 4-[N-nonanoyl-6-aminohexanoyl]benzene sulfonate, 4-[N-decanoyl-6-aminohexanoyl]benzene sulfonate and mixtures thereof; and nonanoyloxy benzene sulfonate together with hydrophilic/hydrophobic bleach formulations can also be used as lime soap peptisers compounds.

Colour Care and Fabric Care Benefits

Technologies which provide a type of colour care benefit can also be included. Examples of these technologies are metallo catalysts for colour maintenance. Such metallo catalysts are described in copending European Patent Application No. 92870181.2. Dye fixing agents, polyolefin dispersion for anti-wrinkles and improved water absorbency, perfume and amino-functional polymer for colour care treatment and perfume substantivity are further examples of colour care/fabric care technologies and are described in the co-pending Patent Application No. 96870140.9, filed Nov. 7, 1996.

Fabric softening agents can also be incorporated into laundry detergent and/or fabric care compositions in accordance with the present invention. These agents may be inorganic or organic in type. Inorganic softening agents are exemplified by the smectite clays disclosed in GB-A-1 400 898 and in U.S. Pat. No. 5,019,292. Organic fabric softening agents include the water insoluble tertiary amines as disclosed in GB-A1 514 276 and EP-B0 011 340 and their combination with mono C12–C14 quaternary ammonium salts are disclosed in EP-B-0 026 527 and EP-B-0 026 528 and di-long-chain amides as disclosed in EP-B-0 242 919. Other useful organic ingredients of fabric softening systems include high molecular weight polyethylene oxide materials as disclosed in EP-A-0 299 575 and 0313 146.

Preferably, the laundry detergent and/or compositions of the present invention will comprise in addition to the modified transferase enzyme, a smectite clay. It has also been surprisingly found that the combination of a modified transferase with a smectite clay provides, refurbishes or restores improved tensile strength, enhanced anti-wrinkle, anti-shrinkage, anti-bobbling properties to fabrics, as well as provide better static control, fabric softness, colour appearance and fabric anti-wear properties and benefits. In addition, improved cleaning benefits are achieved with said combination.

Levels of smectite clay are normally in the range from 2% to 20%, more preferably from 5% to 15% by weight, with the material being added as a dry mixed component to the remainder of the formulation. Organic fabric softening agents such as the water-insoluble tertiary amines or dilong chain amide materials are incorporated at levels of from 0.5% to 5% by weight, normally from 1% to 3% by weight whilst the high molecular weight polyethylene oxide materials and the water soluble cationic materials are added at levels of from 0.1% to 2%, normally from 0.15% to 1.5% by weight. These materials are normally added to the spray dried portion of the composition, although in some instances it may be more convenient to add them as a dry mixed particulate, or spray them as molten liquid on to other solid components of the composition.

Other Surfactants

Ampholytic surfactants are also suitable for use in the laundry detergent and/or fabric care compositions of the present invention. These surfactants can be broadly described as aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. See U.S. Pat. No. 3,929,678 to Laughlin et al., issued Dec. 30, 1975 at column 19, lines 18–35, for examples of ampholytic surfactants. When included therein, the laundry detergent and/or fabric care compositions of the present invention typically comprise from 0.2% to about 15%, preferably from about 1% to about 10% by weight of such ampholytic surfactants.

Zwitterionic surfactants are also suitable for use in laundry detergent and/or fabric care compositions. These surfactants can be broadly described as derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 to Laughlin et al., issued Dec. 30, 1975 at column 19, line 38 through column 22, line 48, for examples of zwitterionic surfactants.

When included therein, the laundry detergent and/or fabric care compositions of the present invention typically comprise from 0.2% to about 15%, preferably from about 1% to about 10% by weight of such zwitterionic surfactants. Semi-polar nonionic surfactants are a special category of nonionic surfactants which include water-soluble amine oxides containing one alkyl moiety of from about 10 to about 18 carbon atoms and 2 moieties selected from the group consisting of alkyl groups and hydroxyalkyl groups containing from about 1 to about 3 carbon atoms; water-soluble phosphine oxides containing one alkyl moiety of from about 10 to about 18 carbon atoms and 2 moieties selected from the group consisting of alkyl groups and hydroxyalkyl groups containing from about 1 to about 3 carbon atoms; and water-soluble sulfoxides containing one alkyl moiety of from about 10 to about 18 carbon atoms and a moiety selected from the group consisting of alkyl and hydroxyalkyl moieties of from about 1 to about 3 carbon atoms. Semi-polar nonionic detergent surfactants include the amine oxide surfactants having the formula

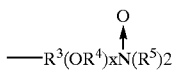

wherein $R^3$ is an alkyl, hydroxyalkyl, or alkyl phenyl group or mixtures thereof containing from about 8 to about 22 carbon atoms; $R^4$ is an alkylene or hydroxyalkylene group containing from about 2 to about 3 carbon atoms or mixtures thereof; x is from 0 to about 3; and each $R^5$ is an alkyl or hydroxyalkyl group containing from about 1 to about 3 carbon atoms or a polyethylene oxide group containing from about 1 to about 3 ethylene oxide groups. The $R^5$ groups can be attached to each other, e.g., through an oxygen or nitrogen atom, to form a ring structure. These amine oxide surfactants in particular include $C_{10}$–$C_{18}$ alkyl dimethyl amine oxides and $C_8$–$C_{12}$ alkoxy ethyl dihydroxy ethyl amine oxides. When included therein, the cleaning compositions of the present invention typically comprise from 0.2% to about 15%, preferably from about 1% to about 10% by weight of such semi-polar nonionic surfactants.

The laundry detergent and/or fabric care composition of the present invention may further comprise a cosurfactant selected from the group of primary or tertiary amines. Suitable primary amines for use herein include amines according to the formula $R_1NH_2$ wherein $R_1$ is a $C_6$–$C_{12}$, preferably $C_6$–$C_{10}$ alkyl chain or $R_4X(CH_2)_n$, X is —O—, —C(O)NH— or —NH—, $R_4$ is a $C_6$–$C_{12}$ alkyl chain n is between 1 to 5, preferably 3. $R_1$ alkyl chains may be straight or branched and may be interrupted with up to 12, preferably less than 5 ethylene oxide moieties. Preferred amines according to the formula herein above are n-alkyl amines. Suitable amines for use herein may be selected from 1-hexylamine, 1-octylamine, 1-decylamine and laurylamine. Other preferred primary amines include C8–C10 oxypropylamine, octyloxypropylamine, 2-ethylhexyl-oxypropylamine, lauryl amido propylamine and amido propylamine.

Suitable tertiary amines for use herein include tertiary amines having the formula $R_1R_2R_3N$ wherein R1 and R2 are $C_1$–$C_8$ alkylchains or

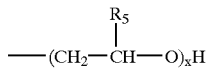

$R_3$ is either a $C_6$–$C_{12}$, preferably $C_6$–$C_{10}$ alkyl chain, or $R_3$ is $R_4X(CH_2)_n$, whereby X is —O—, —C(O)NH— or —NH—, $R_4$ is a $C_4$–$C_{12}$, n is between 1 to 5, preferably 2–3. $R_5$ is H or $C_1$–$C_2$ alkyl and x is between 1 to 6. $R_3$ and $R_4$ may be linear or branched ; $R_3$ alkyl chains may be interrupted with up to 12, preferably less than 5, ethylene oxide moieties.

Preferred tertiary amines are $R_1R_2R_3N$ where R1 is a C6–C12 alkyl chain, R2 and R3 are C1–C3 alkyl or

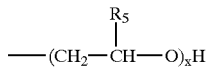

where R5 is H or CH3 and x =1–2.

Also preferred are the amidoamines of the formula:

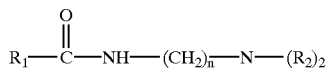

wherein $R_1$ is $C_6$–$C_{12}$ alkyl; n is 2–4, preferably n is 3; $R_2$ and $R_3$ is $C_1$–$C_4$ Most preferred amines of the present invention include 1-octylamine, 1-hexylamine, 1-decylamine, 1-dodecylamine,C8-10oxypropylamine, N coco 1-3diaminopropane, coconutalkyldimethylamine, lauryldimethylamine, lauryl bis(hydroxyethyl)amine, coco bis(hydroxyehtyl)amine, lauryl amine 2 moles propoxylated, octyl amine 2 moles propoxylated, lauryl amidopropyldimethylamine, C8-10 amidopropyldimethylamine and C10 amido-propyldimethylamine. The most preferred amines for use in the compositions herein are 1-hexylamine, 1-octylamine, 1-decylamine, 1-dodecylamine. Especially desirable are n-dodecyldimethylamine and bishydroxyethylcoconutalkylamine and oleylamine 7 times ethoxylated, lauryl amido propylamine and cocoamido propylamine.

Builder System

The laundry detergent and/or fabric care compositions according to the present invention may further comprise a builder system. Any conventional builder system is suitable for use herein including aluminosilicate materials, silicates, polycarboxylates, alkyl- or alkenyl-succinic acid and fatty acids, materials such as ethylenediamine tetraacetate, diethylene triamine pentamethyleneacetate, metal ion sequestrants such as aminopolyphosphonates, particularly ethylenediamine tetramethylene phosphonic acid and diethylene triamine pentamethyienephosphonic acid. Phosphate builders can also be used herein.

Suitable builders can be an inorganic ion exchange material, commonly an inorganic hydrated aluminosilicate material, more particularly a hydrated synthetic zeolite such as hydrated zeolite A, X, B, HS or MAP. Another suitable inorganic builder material is layered silicate, e.g. SKS-6 (Hoechst). SKS-6 is a crystalline layered silicate consisting of sodium silicate ($Na_2Si_2O_5$). Suitable polycarboxylates containing one carboxy group include lactic acid, glycolic acid and ether derivatives thereof as disclosed in Belgian Patent Nos. 831,368, 821,369 and 821,370. Polycarboxylates containing two carboxy groups include the water-soluble salts of succinic acid, malonic acid, (ethylenedioxy) diacetic acid, maleic acid, diglycollic acid, tartaric acid, tartronic acid and fumaric acid, as well as the ether carboxylates described in German Offenlegenschrift 2,446,686, and 2,446,687 and U.S. Pat. No. 3,935,257 and the sulfinyl carboxylates described in Belgian Patent No. 840,623. Polycarboxylates containing three carboxy groups include, in particular, water-soluble citrates, aconitrates and citraconates as well as succinate derivatives such as the carboxymethyloxysuccinates described in British Patent No. 1,379, 241, lactoxysuccinates described in Netherlands Application 7205873, and the oxypolycarboxylate materials such as 2-oxa-1,1,3-propane tricarboxylates described in British Patent No. 1,387,447.

Polycarboxylates containing four carboxy groups include oxydisuccinates disclosed in British Patent No. 1,261,829, 1,1,2,2-ethane tetracarboxylates, 1,1,3,3-propane tetracarboxylates and 1,1,2,3-propane tetracarboxylates. Polycarboxylates containing sulfo substituents include the sulfosuccinate derivatives disclosed in British Patent Nos. 1,398, 421 and 1,398,422 and in U.S. Pat. No. 3,936,448, and the sulfonated pyrolysed citrates described in British Patent No. 1,082,179, while polycarboxylates containing phosphone substituents are disclosed in British Patent No. 1,439,000.

Alicyclic and heterocyclic polycarboxylates include cyclopentane-cis,cis,cis-tetracarboxylates, cyclopentadienide pentacarboxylates, 2,3,4,5-tetrahydro-furan -cis, cis, cis-tetracarboxylates, 2,5-tetrahydro-furan -cis-dicarboxylates, 2,2,5, 5-tetrahydrofuran-tetracarboxylates, 1,2,3,4,5,6-hexane-hexacar-boxylates and and carboxymethyl derivatives of polyhydric alcohols such as sorbitol, mannitol and xylitol. Aromatic poly-carboxylates include mellitic acid, pyromellitic acid and the phthalic acid derivatives disclosed in British Patent No. 1,425,343. Of the above, the preferred polycarboxylates are hydroxycarboxylates containing up to three carboxy groups per molecule, more particularly citrates.

Preferred builder systems for use in the present compositions include a mixture of a water-insoluble aluminosilicate builder such as zeolite A or of a layered silicate (SKS-6), and a water-soluble carboxylate chelating agent such as citric acid.

Preferred builder systems include a mixture of a water-insoluble aluminosilicate builder such as zeolite A, and a watersoluble carboxylate chelating agent such as citric acid. Preferred builder systems for use in liquid laundry detergent and/or fabric care compositions of the present invention are soaps and polycarboxylates.

Other builder materials that can form part of the builder system for use in granular compositions include inorganic materials such as alkali metal carbonates, bicarbonates, silicates, and organic materials such as the organic phosphonates, amino polyalkylene phosphonates and amino polycarboxylates.

Other suitable water-soluble organic salts are the homo- or co-polymeric acids or their salts, in which the polycarboxylic acid comprises at least two carboxyl radicals separated from each other by not more than two carbon atoms. Polymers of this type are disclosed in GB-A-1,596,756. Examples of such salts are polyacrylates of MW 2000–5000 and their copolymers with maleic anhydride, such copolymers having a molecular weight of from 20,000 to 70,000, especially about 40,000.

Detergency builder salts are normally included in amounts of from 5% to 80% by weight of the composition preferably from 10% to 70% and most usually from 30% to 60% by weight.

Chelating Agents

The laundry detergent and/or fabric care compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that the benefit of these materials is due in part to their exceptional ability to remove iron and manganese ions from washing solutions by formation of soluble chelates.

Amino carboxylates useful as optional chelating agents include ethylenediaminetetracetates, N-hydroxyethylethylenediaminetriacetates, nitrilotriacetates, ethylenediamine tetraprionates, triethylenetetraamine-hexacetates, diethylenetriaminepentaacetates, and ethanoldiglycines, alkali metal, ammonium, and substituted ammonium salts therein and mixtures therein.

Amino phosphonates are also suitable for use as chelating agents in the compositions of the invention when at lease low levels of total phosphorus are permitted in laundry detergent and/or fabric care compositions, and include ethylenediaminetetrakis (methylenephosphonates) as DEQUEST. Preferred, these amino phosphonates to not contain alkyl or alkenyl groups with more than about 6 carbon atoms.

Polyfunctionally-substituted aromatic chelating agents are also useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5disulfobenzene.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

The compositions herein may also contain water-soluble methyl glycine diacetic acid (MGDA) salts (or acid form) as a chelant or co-builder useful with, for example, insoluble builders such as zeolites, layered silicates and the like.

If utilized, these chelating agents will generally comprise from about 0.1% to about 15% by weight of the laundry detergent and/or fabric care compositions herein. More preferably, if utilized, the chelating agents will comprise from about 0.1% to about 3.0% by weight of such compositions.

Suds Suppressor

Another optional ingredient is a suds suppressor, exemplified by silicones, and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the suds suppressor is advantageously releasably incorporated in a water-soluble or water-dispersible, substantially non-surface-active detergent impermeable carrier. Alternatively the suds suppressor can be dissolved or dispersed in a liquid carrier and applied by spraying on to one or more of the other components. A preferred silicone suds controlling agent is disclosed in Bartollota et al. U.S. Pat. No. 3 933 672. Other particularly useful suds suppressors are the self-emulsifying silicone suds suppressors, described in German Patent Application DTOS 2 646 126 published Apr. 28, 1977. An example of such a compound is DC-544, commercially available from Dow Corning, which is a siloxane-glycol copolymer. Especially preferred suds controlling agent are the suds suppressor system comprising a mixture of silicone oils and 2-alkyl-alcanols. Suitable 2-alkyl-alkanols are 2-butyl-octanol which are commercially available under the trade name Isofol 12 R. Such suds suppressor system are described in Copending European Patent application N 92870174.7 filed Nov. 10, 1992. Especially preferred silicone suds controlling agents are described in Copending European Patent application No.92201649.8. Said compositions can comprise a silicone/silica mixture in combination with fumed nonporous silica such as Aerosil$^R$.

The suds suppressors described above are normally employed at levels of from 0.001% to 2% by weight of the composition, preferably from 0.01% to 1% by weight.

Preservatives

The laundry detergent and/or fabric care compositions herein may also optionally contain one or more preservatives. The function of the preservatives is to prevent organisms/micro-organisms from breeding and growing in the laundry detergent and/or fabric care composition and on the fabrics treated with the compositions herein. In the absence of such preservatives, organisms/micro-organisms could grow on the fabrics treated with the laundry detergent and/or fabric care compositions herein because a significant amount of carbohydrates/sugar could remain on the fabrics after treatment.

Sanitization of fabrics can be achieved by the compositions of the present invention containing antimicrobial materials, e.g., antibacterial halogenated compounds, quaternary compounds, and phenolic compounds. Suitable preservatives for use with the present invention include, but are not limited to, the following. It is preferable to use a broad spectrum preservative, e.g., one that is effective on both bacteria (both gram positive and gram negative) and fungi. A limited spectrum preservative, e.g., one that is only effective on a single group of microorganisms, e.g., fungi, can be used in combination with a broad spectrum preservative or other limited spectrum preservatives with complimentary and/or supplementary activity. A mixture of broad spectrum preservatives can also be used. In some cases where a specific group of microbial contaminants is problematic (such as Gram negatives), aminocarboxylate chelators may be used alone or as potentiators in conjunction with other preservatives. These chelators which include, e.g., ethylenediaminetetraacetic acid (EDTA), hydroxyethylenediaminetriacetic acid, diethylenetriaminepentaacetic acid, and other aminocarboxylate chelators, and mixtures thereof, and their salts, and mixtures thereof, can increase preservative effectiveness against Gram-negative bacteria, especially Pseudomonas species.

Antimicrobial preservatives useful in the present invention include biocidal compounds, i.e., substances that kill microorganisms, or biostatic compounds, i.e., substances that inhibit and/or regulate the growth of microorganisms.

(1). Organic Sulfur Compounds

Preferred water-soluble preservatives for use in the present invention are organic sulfur compounds. Some non-limiting examples of organic sulfur compounds suitable for use in the present invention are:

(a) 3-Isothiazolone Compounds

A preferred preservative is an antimicrobial, organic preservative containing 3-isothiazolone groups having the formula:

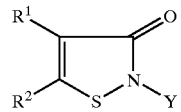

wherein

Y is an unsubstituted alkyl, alkenyl, or alkynyl group of from about 1 to about 18 carbon atoms, an unsubstituted or substituted cycloalkyl group having from about a 3 to about a 6 carbon ring and up to 12 carbon atoms, an unsubstituted or substituted aralkyl group of up to about 10 carbon atoms, or an unsubstituted or substituted aryl group of up to about 10 carbon atoms;

$R^1$ is hydrogen, halogen, or a $(C_1-C_4)$ alkyl group; and $R^2$ is hydrogen, halogen, or a $(C_1-C_4)$ alkyl group.

Preferably, when Y is methyl or ethyl, $R^1$ and $R^2$ should not both be hydrogen. Salts of these compounds formed by reacting the compound with acids such as hydrochloric, nitric, sulfuric, etc. are also suitable. This class of compounds is disclosed in U.S. Pat. No. 4,265,899, Lewis et al., issued May 5, 1981, and incorporated herein by reference. Examples of said compounds are: 5-chloro-2-methyl4-isothiazolin-3-one; 2-n-butyl-3-isothiazolone; 2-benzyl-3-isothiazolone; 2-phenyl-3-isothiazolone, 2-methyl-4,5-dichloroisothiazolone; 5-chloro-2-methyl-3-isothiazolone; 2-methyl-4-isothiazolin-3-one; and mixtures thereof. A preferred preservative is a water-soluble mixture of 5-chloro-2-methyl-4-isothiazolin-3-one and 2-methyl-4-isothiazolin-3-one, more preferably a mixture of about 77% 5-chloro-2-methyl-4-isothiazolin-3-one and about 23% 2-methyl-4-isothiazolin-3-one, a broad spectrum preservative available as a 1.5% aqueous solution under the trade name Kathon® CG by Rohm and Haas Company. When Kathon® is used as the preservative in the present invention it is present at a level of from about 0.0001% to about 0.01%, preferably from about 0.0002% to about 0.005%, more preferably from about 0.0003% to about 0.003%, most preferably from about 0.0004% to about 0.002%, by weight of the composition.

Other isothiazolins include 1,2-benzisothiazolin-3-one, available under the trade name Proxel® products; and 2-methyl-4,5-trimethylene4-isothiazolin-3-one, available under the trade name Promexal®. Both Proxel and Promexal are available from Zeneca. They have stability over a wide pH range (i.e., 4–12). Neither contain active halogen and are not formaldehyde releasing preservatives. Both Proxel and Promexal are effective against typical Gram negative and positive bacteria, fungi and yeasts when used at a level from about 0.001% to about 0.5%, preferably from about 0.005% to about 0.05%, and most preferably from about 0.01% to about 0.02% by weight of the usage composition.

(b) Sodium Pyrithione

Another preferred organic sulfur preservative is sodium pyrithione, with water solubility of about 50%. When sodium pyrithione is used as the preservative in the present invention it is typically present at a level of from about 0.0001% to about 0.01%, preferably from about 0.0002% to about 0.005%, more preferably from about 0.0003% to about 0.003%, by weight of the usage composition. Mixtures of the preferred organic sulfur compounds can also be used as the preservative in the present invention.

(2). Halogenated Compounds

Preferred preservatives for use in the present invention are halogenated compounds. Some non-limiting examples of halogenated compounds suitable for use in the present invention are:

5-bromo-5-nitro-1,3-dioxane, available under the trade name Bronidox L® from Henkel. Bronidox L® has a solubility of about 0.46% in water. When Bronidox is used as the preservative in the present invention it is typically present at a level of from about 0.0005% to about 0.02%, preferably from about 0.001% to about 0.01%, by weight of the usage composition;

2-bromo-2-nitropropane-1,3-diol, available under the trade name Bronopol® from Inolex can be used as the preservative in the present invention. Bronopol has a solubility of about 25% in water. When Bronopol is used as the preservative in the present invention it is typically present at a level of from about 0.002% to about 0.1%, preferably from about 0.005% to about 0.05%, by weight of the usage composition;

1,1'-hexamethylene bis(5-(p-chlorophenyl)biguanide), commonly known as chlorhexidine, and its salts, e.g., with acetic and gluconic acids can be used as a preservative in the present invention. The digluconate salt is highly water-soluble, about 70% in water, and the diacetate salt has a solubility of about 1.8% in water. When chlorohexidine is used as the preservative in the present invention it is typically present at a level of from about 0.0001% to about 0.04%, preferably from about 0.0005% to about 0.01%, by weight of the usage composition.

1,1,1-Trichloro-2-methylpropan-2-ol, commonly known as chlorobutanol, with water solubility of about 0.8%; a typical effective level of chlorobutanol is from about 0.1% to about 0.5%, by weight of the usage composition. 4,4'-(Trimethylenedioxy)bis-(3-bromobenzamidine)diisethionate, or dibromopropamidine, with water solubility of about 50%; when dibromopropamidine is used as the preservative in the present invention it is typically present at a level of from about 0.0001% to about 0.05%, preferably from about 0.0005% to about 0.01% by weight of the usage composition.

Mixtures of the preferred halogenated compounds can also be used as the preservative in the present invention.

(3). Cyclic Organic Nitrogen Compounds

Preferred water-soluble preservatives for use in the present invention are cyclic organic nitrogen compounds. Some non-limiting examples of cyclic organic nitrogen compounds suitable for use in the present invention are:

(a) Imidazolidinedione Compounds

Preferred preservatives for use in the present invention are imidazolidione compounds. Some non-limiting examples of imidazolidinedione compounds suitable for use in the present invention are:

1,3-bis(hydroxymethyl)-5,5-dimethyl-2,4-imidazolidinedione, commonly known as dimethyloldimethylhydantoin, or DMDM hydantoin, available as, e.g., Glydant® from Lonza. DMDM hydantoin has a water solubility of more than 50% in water, and is mainly effective on bacteria. When DMDM hydantoin is used, it is preferable that it be used in combination with a broad spectrum preservative such as Kathon CG®, or formaldehyde. A preferred mixture is about a 95:5 DMDM hydantoin to 3-butyl-2-iodopropynylcarbamate mixture, available under the trade name Glydant Plus® from Lonza. When Glydant Plus® is used as the preservative in the present invention, it is typically present at a level of from about 0.005% to about 0.2% by weight of the usage composition;

N-[1,3-bis(hydroxymethyl)2,5-dioxo-4-imidazolidinyl]-N,N'-bis(hydroxymethyl)urea, commonly known as diazolidinyl urea, available under the trade name GermaII II® from Sutton Laboratories, Inc. (Sutton) can be used as the preservative in the present invention. When GermaII II® is used as the preservative in the present invention, it is typically present at a level of from about 0.01% to about 0.1% by weight of the usage composition;

N,N"-methylenebis{N'-[1-(hydroxymethyl)-2, 5-dioxo-4-imidazolidinyl]urea}, commonly known as imidazolidinyl urea, available, e.g., under the trade name Abiol® from 3V-Sigma, Unicide U-13® from Induchem, GermaII 115® from (Sutton) can be used as the preservative in the present invention. When imidazolidinyl urea is used as the preservative, it is typically present at a level of from about 0.05% to about 0.2%, by weight of the usage composition.

Mixtures of the preferred imidazolidinedione compounds can also be used as the preservative in the present invention.

(b) Polymethoxy Bicyclic Oxazolidine

Another preferred water-soluble cyclic organic nitrogen preservative is polymethoxy bicyclic oxazolidine, having the general formula:

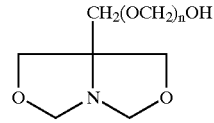

where n has a value of from about 0 to about 5, and is available under the trade name Nuosept® C from Hüls America. When Nuosept® C is used as the preservative, it is typically present at a level of from about 0.005% to about 0.1%, by weight of the usage composition.

Mixtures of the preferred cyclic organic nitrogen compounds can also be used as the preservative in the present invention.

(4). Low Molecular Weight Aldehydes (a). Formaldehyde

A preferred preservative for use in the present invention is formaldehyde. Formaldehyde is a broad spectrum preservative which is normally available as formalin which is a 37% aqueous solution of formaldehyde. When formaldehyde is used as the preservative in the present invention, typical levels are from about 0.003% to about 0.2%, preferably from about 0.008% to about 0.1%. more preferably from about 0.01% to about 0.05%, by weight of the usage composition.

(b) Glutaraldehyde

A preferred preservative for use in the present invention is glutaraldehyde. Glutaraldehyde is a water-soluble, broad spectrum preservative commonly available as a 25% or a 50% solution in water. When glutaraldehyde is used as the preservative in the present invention it is typically present at a level of from about 0.005% to about 0.1%, preferably from about 0.01% to about 0.05%, by weight of the usage composition.

(5). Quaternary Compounds

Preferred preservatives for use in the present invention are cationic and/or quaternary compounds. Such compounds include polyaminopropyl biguanide, also known as polyhexamethylene biguanide having the general formula:

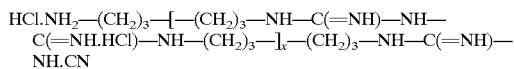

Polyaminopropyl biguanide is a water-soluble, broad spectrum preservative which is available as a 20% aqueous solution available under the trade name Cosmocil CQ® from ICI Americas, Inc., or under the trade name Mikrokill® from Brooks, Inc.

1-(3-Chlorallyl)-3,5,7-triaza-1-azoniaadamantane chloride, available, e.g., under the trade name Dowicil 200 from Dow Chemical, is an effective quaternary ammonium preservative; it is freely soluble in water; however, it has the tendency to discolor (yellow), therefore it is not highly preferred. Mixtures of the preferred quaternary ammonium compounds can also be used as the preservative in the present invention. When quaternary ammonium compounds are used as the preservative in the present invention, they are typically present at a level of from about 0.005% to about 0.2%, preferably from about 0.01% to about 0.1%, by weight of the usage composition.

(6). Dehydroacetic Acid

A preferred preservative for use in the present invention is dehydroacetic acid. Dehydroacetic acid is a broad spectrum preservative preferably in the form of a sodium or a potassium salt so that it is water-soluble. This preservative acts more as a biostatic preservative than a biocidal preservative. When dehydroacetic acid is used as the preservative it is typically used at a level of from about 0.005% to about 0.2%, preferably from about 0.008% to about 0.1%, more preferably from about 0.01% to about 0.05%, by weight of the usage composition.

(7). Phenyl and Phenolic Compounds

Some non-limiting examples of phenyl and phenolic compounds suitable for use in the present invention are:

4,4'-diamidino-α,ω-diphenoxypropane diisethionate, commonly known as propamidine isethionate, with water solubility of about 16%; and 4,4'-diamidino-α, ω-diphenoxyhexane diisethionate, commonly known as hexamidine isethionate. Typical effective level of these salts is about 0.0002% to about 0.05% by weight of the usage composition. Other examples are benzyl alcohol, with a water solubility of about 4%; 2-phenylethanol, with a water solubility of about 2%; and 2-phenoxyethanol, with a water solubility of about 2.67%; typical effective level of these phenyl and phenoxy alcohol is from about 0.1% to about 0.5%, by weight of the usage composition.

(8) Mixtures thereof

It is preferred that no, or essentially no, volatile low molecular weight monohydric alcohols such as ethanol and/or isopropanol are intentionally added to the composition of the present invention since these volatile organic compounds will contribute both to flammability problems and environmental pollution problems. If small amounts of low molecular weight monohydric alcohols are present in the composition of the present invention due to the addition of these alcohols to such things as perfumes and as stabilizers for some preservatives, it is preferable that the level of monohydric alcohol be less than about 5%, preferably less than about 3%, more preferably less than about 1%.

(9). Mixtures thereof

The preservatives of the present invention can be used in mixtures in order to control a broad range of microorganisms. Bacteriostatic effects can sometimes be obtained for aqueous compositions by adjusting the composition pH to an acid pH, e.g., less than about pH 4, preferably less than about pH 3, or a basic pH, e.g., greater than about 10, preferably greater than about 11.

(10). Preferred Preservatives

Preferably the preservatives used in the compositions of the present invention are selected from the group consisting of: isothiazolones; bronopol; hydantoins; oxazolidines; glutaraldehyde; isethionates; quats (benzalkoniums); and mixtures thereof.

Others

Other components such as soil-suspending agents, soil-release agents, optical brighteners, abrasives, bactericides, tarnish inhibitors, coloring agents, and/or encapsulated or non-encapsulated perfumes may be employed.

Especially suitable encapsulating materials are water soluble capsules which consist of a matrix of polysaccharide and polyhydroxy compounds such as described in GB 1,464,616.

Other suitable water soluble encapsulating materials comprise dextrins derived from ungelatinized starch acid-esters of substituted dicarboxylic acids such as described in U.S. Pat. No. 3,455,838. These acid-ester dextrins are,preferably, prepared from such starches as waxy maize, waxy sorghum, sago, tapioca and potato. Suitable examples of said encapsulating materials include N-Lok manufactured by National Starch. The N-Lok encapsulating material consists of a modified maize starch and glucose. The starch is modified by adding monofunctional substituted groups such as octenyl succinic acid anhydride.

Antiredeposition and soil suspension agents suitable herein include cellulose derivatives such as methylcellulose, carboxymethylcellulose and hydroxyethylcellulose, and homo- or co-polymeric polycarboxylic acids or their salts. Polymers of this type include the polyacrylates and maleic anhydride-acrylic acid copolymers previously mentioned as builders, as well as copolymers of maleic anhydride with ethylene, methylvinyl ether or methacrylic acid, the maleic anhydride constituting at least 20 mole percent of the copolymer. These materials are normally used at levels of from 0.5% to 10% by weight, more preferably from 0.75% to 8%, most preferably from 1% to 6% by weight of the composition.

Preferred optical brighteners are anionic in character, examples of which are disodium 4,4'-bis-(2-diethanolamino-4-anilino-s-triazin-6-ylamino)stilbene-2:2'disulphonate, disodium 4,-4'-bis-(2-morpholino4-anilino-s-triazin-6-ylamino-stilbene-2:2'-disulphonate, disodium 4,4'-bis-(2,4-dianilino-s-triazin-6-ylamino)stilbene-2:2'-disulphonate, monosodium 4',4"-bis-(2,4-dianilino-s-triazin-6 ylamino) stilbene-2-sulphonate, disodium 4,4'-bis-(2-anilino-4-(N-methyl-N-2-hydroxyethylamino)-s-triazin-6-ylamino) stilbene-2,2'-disulphonate, di-sodium 4,4'-bis-(4-phenyl-2, 1,3-triazol-2-yl)-stilbene-2,2'disulphonate, di-sodium 4,4'bis(2-anilino-4-(1-methyl-2-hydroxyethylamino)-s-triazin6-ylami-no)stilbene-2,2'disulphonate, sodium 2(stilbyl4"-(naphtho-1',2':4,5)-1,2,3 -triazole-2"-sulphonate and 4,4'-bis(2-sulphostyryl)biphenyl. Highly preferred brighteners are the specific brighteners of copending European Patent application No. 95201943.8.

Other useful polymeric materials are the polyethylene glycols, particularly those of molecular weight 1000–10000, more particularly 2000 to 8000 and most preferably about 4000. These are used at levels of from 0.20% to 5% more preferably from 0.25% to 2.5% by weight. These polymers and the previously mentioned home or co-polymeric polycarboxylate salts are valuable for improving whiteness maintenance, fabric ash deposition, and cleaning performance on clay, proteinaceous and oxidizable soils in the presence of transition metal impurities.

Soil release agents useful in compositions of the present invention are conventionally copolymers or terpolymers of terephthalic acid with ethylene glycol and/or propylene glycol units in various arrangements. Examples of such polymers are disclosed in the commonly assigned U.S. Pat. Nos. 4116885 and 4,711,730 and European Published Patent Application No. 0 272 033. A particular preferred polymer in accordance with EP-A-0 272 033 has the formula

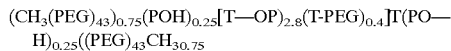

$(CH_3(PEG)_{43})_{0.75}(POH)_{0.25}[T—OP]_{2.8}(T-PEG)_{0.4}]T(PO—H)_{0.25}((PEG)_{43}CH_{30.75}$ where PEG is $—(OC_2H_4)O—$, PO is $(OC_3H_6O)$ and T is $(pcOC_6H_4CO)$.

Also very useful are modified polyesters as random copolymers of dimethyl terephthalate, dimethyl sulfoisophthalate, ethylene glycol and 1–2 propane diol, the end groups consisting primarily of sulphobenzoate and secondarily of mono esters of ethylene glycol and/or propane-diol. The target is to obtain a polymer capped at both end by sulphobenzoate groups, "primarily", in the present context most of said copolymers herein will be end-capped by sulphobenzoate groups. However, some copolymers will be less than fully capped, and therefore their end groups may consist of monoester of ethylene glycol and/or propane 1–2 diol, thereof consist "secondarily" of such species.

The selected polyesters herein contain about 46% by weight of dimethyl terephthalic acid, about 16% by weight of propane -1.2 diol, about 10% by weight ethylene glycol about 13% by weight of dimethyl sulfobenzoic acid and about 15% by weight of sulfoisophthalic acid, and have a molecular weight of about 3.000. The polyesters and their method of preparation are described in detail in EPA 311 342.

It is well-known in the art that free chlorine in tap water rapidly deactivates the enzymes comprised in laundry detergent and/or fabric care compositions. Therefore, using chlorine scavenger such as perborate, ammonium sulfate, sodium sulphite or polyethyleneimine at a level above 0.1% by weight of total composition, in the formulas will provide improved through the wash stability of the detergent enzymes. Compositions comprising chlorine scavenger are described in the European patent application 92870018.6 filed Jan. 31, 1992.

Alkoxylated polycarboxylates such as those prepared from polyacrylates are useful herein to provide additional grease removal performance. Such materials are described in WO 91/08281 and PCT 90/01815 at p. 4 et seq., incorporated herein by reference. Chemically, these materials comprise polyacrylates having one ethoxy side-chain per every 7–8 acrylate units. The side-chains are of the formula $—(CH_2CH_2O)_m(CH_2)_nCH_3$ wherein m is 2–3 and n is 6–12. The side-chains are ester-linked to the polyacrylate "backbone" to provide a "comb" polymer type structure. The molecular weight can vary, but is typically in the range of about 2000 to about 50,000. Such alkoxylated polycarboxylates can comprise from about 0.05% to about 10%, by weight, of the compositions herein.

Method of Washing

The laundry detergent and/or fabric care compositions of the invention may be used in essentially any washing, cleaning and/or fabric care methods, including soaking methods, pre-treatment methods, methods with rinsing steps for which a separate rinse aid composition may be added and post-treatment methods. An example of pre-treatment would consist of treating the fabric with a pre-treatment composition comprising a transferase and/or its corresponding enzymatic substrate. This step can be achieved already in the washing machine or in a basin or this pre-treatment composition can be sprayed onto the fabric. Optionally, the pre-treated fabric is dried and is then washed/treated with a conventional laundry detergent and/or fabric care composition (not comprising the transferase nor the substrate of the present invention). An example of post-treatment would consist of washing/treating the fabric with a conventional laundry detergent and/or fabric care composition (not comprising the transferase nor the substrate of the present invention). Optionally, the fabric can be dried. The fabric would then be treated with a post-treatment composition comprising a transferase and/or its corresponding enzymatic substrate. The transferase enzyme and/or its corresponding enzymatic substrate can also be incorporated in a rinsing composition which is used at the end of a washing cycle. In another example, the enzyme and the substrate can be comprised in different compositions and/or added at different steps. For example, the pre-treatment or post-treatment composition comprises exclusively the transferase enzyme or its corresponding enzymatic substrate and the conventional laundry detergent and/or fabric care composition comprises exclusively the corresponding enzymatic substrate or the transferase enzyme.

The process described herein comprises contacting fabrics with a laundering solution in the usual manner and exemplified hereunder. The process of the invention is conveniently carried out in the course of the cleaning process. The method of cleaning is preferably carried out at 5° C. to 95° C., especially between 10° C. and 60° C. The pH of the treatment solution is preferably from 7 to 12.

The following examples are meant to exemplify compositions of the present invention, but are not necessarily meant to limit or otherwise define the scope of the invention.

In the laundry detergent and/or fabric care compositions, the enzymes levels are expressed by pure enzyme by weight of the total composition and unless otherwise specified, the detergent ingredients are expressed by weight of the total compositions. The abbreviated component identifications therein have the following meanings:

| | |
|---|---|
| LAS | Sodium linear $C_{11–13}$ alkyl benzene sulphonate. |
| TAS | Sodium tallow alkyl sulphate. |
| CxyAS | Sodium $C_{1x}$–$C_{1y}$ alkyl sulfate. |
| CXySAS | Sodium $C_{1x}$–$C_{1y}$ secondary (2,3) alkyl sulfate. |
| CxyEz | $C_{1x}$–$C_{1y}$ predominantly linear primary alcohol condensed with an average of z moles of ethylene oxide. |

-continued

| | |
|---|---|
| CxyEzS | $C_{1x}$–$C_{1y}$ sodium alkyl sulfate condensed with an average of z moles of ethylene oxide. |
| QAS | $R_2 \cdot N + (CH_3)_2(C_2H_4OH)$ with $R_2 = C_{12}$–$C_{14}$. |
| QAS 1 | $R_2 \cdot N + (CH_3)_2(C_2H_4OH)$ with $R_2 = C_8$–$C_{11}$. |
| APA | $C_{8-10}$ amido propyl dimethyl amine. |
| Soap | Sodium linear alkyl carboxylate derived from a 80/20 mixture of tallow and coconut fatty acids. |
| STS | Sodium toluene sulphonate. |
| CFAA | $C_{12}$–$C_{14}$ alkyl N-methyl glucamide. |
| TFAA | $C_{16}$–$C_{18}$ alkyl N-methyl glucamide. |
| TPKFA | $C_{12}$–$C_{14}$ topped whole cut fatty acids. |
| DEQA | Di-(tallow-oxy-ethyl) dimethyl ammonium chloride. |
| DEQA (2) | Di-(soft-tallowyloxyethyl) hydroxyethyl methyl ammonium methylsulfate. |
| DTDMAMS | Ditallow dimethyl ammonium methylsulfate. |
| SDASA | 1:2 ratio of stearyldimethyl amine:triple-pressed stearic acid. |
| Silicate | Amorphous Sodium Silicate ($SiO_2$:$Na_2O$ ratio = 1,6-3.2). |
| Zeolite A | Hydrated Sodium Aluminosilicate of formula $Na_{12}(AlO_2SiO_2)_{12} \cdot 27H_2O$ having a primary particle size in the range from 0.1 to 10 micrometers (Weight expressed on an anhydrous basis). |
| Na-SKS-6 | Crystalline layered silicate of formula $\delta$-$Na_2Si_2O_5$. |
| Citrate | Tri-sodium citrate dihydrate of activity 86.4% with a particle size distribution between 425 and 850 micrometers. |
| Citric | Anhydrous citric acid. |
| Borate | Sodium borate |
| Carbonate | Anhydrous sodium carbonate with a particle size between 200 and 900 micrometers. |
| Bicarbonate | Anhydrous sodium hydrogen carbonate with a particle size distribution between 400 and 1200 micrometers. |
| Sulphate | Anhydrous sodium sulphate. |
| Mg Sulphate | Anhydrous magnesium sulfate. |
| STPP | Sodium tripolyphosphate. |
| TSPP | Tetrasodium pyrophosphate. |
| MA/AA | Random copolymer of 4:1 acrylate/maleate, average molecular weight about 70,000–80,000. |
| MA/AA 1 | Random copolymer of 6:4 acrylate/maleate, average molecular weight about 10,000. |
| AA | Sodium polyacrylate polymer of average molecular weight 4,500. |
| PB1 | Anhydrous sodium perborate monohydrate of nominal formula $NaBO_2.H_2O_2$. |
| PB4 | Sodium perborate tetrahydrate of nominal formula $NaBO_2.3H_2O.H_2O_2$. |
| Percarbonate | Anhydrous sodium percarbonate of nominal formula $2Na_2CO_3.3H_2O_2$. |
| TAED | Tetraacetylethylenediamine. |
| NOBS | Nonanoyloxybenzene sulfonate in the form of the sodium salt. |
| NACA-OBS | (6-nonamidocaproyl) oxybenzene sulfonate. |
| DTPA | Diethylene triamine pentaacetic acid. |
| HEDP | 1,1-hydroxyethane diphosphonic acid. |
| DETPMP | Diethyltriamine penta (methylene) phosphonate, marketed by Monsanto under the Trade name Dequest 2060. |
| EDDS | Ethylenediamine-N,N'-disuccinic acid, (S,S) isomer in the form of its sodium salt |
| Photoactivated Bleach | Sulfonated zinc phtalocyanine encapsulated in dextrin soluble polymer. |
| Photoactivated Bleach 1 | Sulfonated alumino phtalocyanine encapsulated in dextrin soluble polymer. |
| Protease | Proteolytic enzyme sold under the tradename Savinase, Alcalase, Durazym by Novo Nordisk A/S, Maxacal, Maxapem sold by Gist-Brocades and proteases described in patents WO91/06637 and/or WO95/10591 and/or EP 251 446. |
| Amylase | Amylolytic enzyme sold under the tradename Purafact Ox $Am^R$ described in WO 94/18314, WO96/05295 sold by Genencor; Termamyl ®, Fungamyl ® and Duramyl ®, all available from Novo Nordisk A/S and those described in WO95/26397. |
| Lipase | Lipolytic enzyme sold under the tradename Lipolase, Lipolase Ultra by Novo Nordisk A/S and Lipomax by Gist-Brocades. |
| CBD- transferase | Transferase EC 2.4.1.5 sold by Sigma under the tradename dextransucrase; Transferase EC 2.3.2.13 available from Novo Nordisk A/S under the tradename Transglutaminase and/or Transferase EC 2.4.1.19 sold by Novo Nordisk A/S under the tradename Toruzyme; linked by $PEG(NPC)_2$ MW 3400 from Sigma to the CBD Cellulozome from *Clostridium cellulovorans*, sold under the tradename Cellulose Binding Domain by Sigma; and/or Transferase EC 2.4.1.5 sold by Sigma under the tradename dextransucrase, linked by the Humicola Insolens family 45 cellulase linker to the CBD of the cellulytic enzyme sold under the tradename Carezyme by Novo Nordisk A/S. |
| Substrate | Maltose, e.g. Maltose M5885 sold by Sigma and/or starch, e.g. YES2760 sold by Sigma; an amino acid, di/tri/polypeptide and/or protein and/or cycodextrin ($\alpha$, $\beta$, $\gamma$) and/or sucrose. |
| Cellulase | Cellulytic enzyme sold under the tradename Carezyme, Celluzyme and/or Endolase by Novo Nordisk A/S. |
| CMC | Sodium carboxymethyl cellulose. |
| PVP | Polyvinyl polymer, with an average molecular weight of 60,000. |
| PVNO | Polyvinylpyridine-N-Oxide, with an average molecular weight of 50,000. |
| PVPVI | Copolymer of vinylimidazole and vinylpyrrolidone, with an average molecular weight of 20,000. |
| Brightener 1 | Disodium 4,4'-bis(2-sulphostyryl)biphenyl. |
| Brightener 2 | Disodium 4,4'-bis(4-anilino-6-morpholino-1.3.5-triazin-2-yl) stilbene-2:2'-disulfonate. |
| Silicone antifoam | Polydimethylsiloxane foam controller with siloxane-oxyalkylene copolymer as dispersing agent with a ratio of said foam controller to said dispersing agent of 10:1 to 100:1. |
| Suds Suppressor | 12% Silicone/silica, 18% stearyl alcohol, 70% starch in granular form. |
| Opacifier | Water based monostyrene latex mixture, sold by BASF Aktiengesellschaft under the tradename Lytron 621. |
| SRP 1 | Anionically end capped poly esters. |
| SRP 2 | Diethoxylated poly (1,2 propylene terephtalate) short block polymer. |
| QEA | $bis((C_2H_5O)(C_2H_4O)_n)(CH_3)$—$N^+$—$C_6H_{12}$—$N^+$—$(CH_3)$ $bis((C_2H_5O)$—$(C_2H_4O))_n$, wherein n from 20 to 30. |
| PEI | Polyethyleneimine with an average molecular weight of 1800 and an average ethoxylation degree of 7 ethyleneoxy residues per nitrogen. |
| SCS | Sodium cumene sulphonate. |
| HMWPEO | High molecular weight polyethylene oxide. |
| PEGx | Polyethylene glycol, of a molecular weight of x. |
| PEO | Polyethylene oxide, with an average molecular weight of 5,000. |
| TE PAE | Tetreaethylenepentaamine ethoxylate. |

EXAMPLE 1

The following high density laundry detergent compositions were prepared according to the present invention:

|  | I | II | III | IV | V | VI |
|---|---|---|---|---|---|---|
| LAS | 8.0 | 8.0 | 8.0 | 2.0 | 6.0 | 6.0 |
| TAS | — | 0.5 | — | 0.5 | 1.0 | 0.1 |
| C46(S)AS | 2.0 | 2.5 | — | — | — | — |
| C25AS | — | — | — | 7.0 | 4.5 | 5.5 |
| C68AS | 2.0 | 5.0 | 7.0 | — | — | — |
| C25E5 | — | — | 3.4 | 10.0 | 4.6 | 4.6 |
| C25E7 | 3.4 | 3.4 | 1.0 | — | — | — |
| C25E3S | — | — | — | 2.0 | 5.0 | 4.5 |
| QAS | — | 0.8 | — | — | — | — |
| QAS 1 | — | — | — | 0.8 | 0.5 | 1.0 |
| Zeolite A | 18.1 | 18.0 | 14.1 | 18.1 | 20.0 | 18.1 |
| Citric | — | — | — | 2.5 | — | 2.5 |
| Carbonate | 13.0 | 13.0 | 27.0 | 10.0 | 10.0 | 13.0 |
| Na-SKS-6 | — | — | — | 10.0 | — | 10.0 |
| Silicate | 1.4 | 1.4 | 3.0 | 0.3 | 0.5 | 0.3 |
| Citrate | — | 1.0 | — | 3.0 | — | — |
| Sulfate | 26.1 | 26.1 | 26.1 | 6.0 | — | — |
| Mg sulfate | 0.3 | — | — | 0.2 | — | 0.2 |
| MA/AA | 0.3 | 0.3 | 0.3 | 4.0 | 1.0 | 1.0 |
| CMC | 0.2 | 0.2 | 0.2 | 0.2 | 0.4 | 0.4 |
| PB4 | 9.0 | 9.0 | 5.0 | — | — | — |
| Percarbonate | — | — | — | — | 18.0 | 18.0 |
| TAED | 1.5 | 0.4 | 1.5 | — | 3.9 | 4.2 |
| NACA-OBS | — | 2.0 | 1.0 | — | — | — |
| DETPMP | 0.25 | 0.25 | 0.25 | 0.25 | — | — |
| SRP 1 | — | — | — | 0.2 | — | 0.2 |
| EDDS | — | 0.25 | 0.4 | — | 0.5 | 0.5 |
| CFAA | — | 1.0 | — | 2.0 | — | — |
| HEDP | 0.3 | 0.3 | 0.3 | 0.3 | 0.4 | 0.4 |
| QEA | — | — | — | 0.2 | — | 0.5 |
| CBD-transferase | 1.0 | 0.1 | 0.05 | 0.02 | 0.1 | 0.5 |
| Substrate | 0.1 | — | 5.0 | — | 10.0 | 15.0 |
| Protease | 0.009 | 0.009 | 0.01 | 0.04 | 0.05 | 0.03 |
| Amylase | 0.002 | 0.002 | 0.002 | 0.006 | 0.008 | 0.008 |
| Cellulase | 0.0007 | — | — | 0.0007 | 0.0007 | 0.0007 |
| Lipase | 0.006 | — | — | 0.01 | 0.01 | 0.01 |
| Photoactivated bleach (ppm) | 15 | 15 | 15 | — | 20 | 20 |
| PVNO/PVPVI | — | — | — | 0.1 | — | — |
| Brightener 1 | 0.09 | 0.09 | 0.09 | — | 0.09 | 0.09 |
| Perfume | 0.3 | 0.3 | 0.3 | 0.4 | 0.4 | 0.4 |
| Silicone antifoam | 0.5 | 0.5 | 0.5 | — | 0.3 | 0.3 |
| Density in g/liter | 850 | 850 | 850 | 850 | 850 | 850 |
| Miscellaneous and minors |  |  | Up to 100% |  |  |  |

EXAMPLE 2

The following granular laundry detergent compositions of particular utility under European machine wash conditions were prepared according to the present invention:

|  | I | II | III | IV | V | VI |
|---|---|---|---|---|---|---|
| LAS | 5.5 | 7.5 | 5.0 | 5.0 | 6.0 | 7.0 |
| TAS | 1.25 | 1.9 | — | 0.8 | 0.4 | 0.3 |
| C24AS/C25AS | — | 2.2 | 5.0 | 5.0 | 5.0 | 2.2 |
| C2SE3S | — | 0.8 | 1.0 | 1.5 | 3.0 | 1.0 |
| C45E7 | 3.25 | — | — | — | — | 3.0 |
| TFAA | — | — | 2.0 | — | — | — |
| C25E5 | — | 5.5 | — | — | — | — |
| QAS | 0.8 | — | — | — | — | — |
| QAS 1 | — | 0.7 | 1.0 | 0.5 | 1.0 | 0.7 |
| STPP | 19.7 | — | — | — | — | — |
| Zeolite A | — | 19.5 | 25.0 | 19.5 | 20.0 | 17.0 |
| NaSKS-6/citric acid (79:21) | — | 10.6 | — | 10.6 | — | — |
| Na-SKS-6 | — | — | 9.0 | — | 10.0 | 10.0 |
| Carbonate | 6.1 | 21.4 | 9.0 | 10.0 | 10.0 | 18.0 |
| Bicarbonate | — | 2.0 | 7.0 | 5.0 | — | 2.0 |
| Silicate | 6.8 | — | — | 0.3 | 0.5 | — |
| Citrate | — | — | 4.0 | 4.0 | — | — |
| Sulfate | 39.8 | — | — | 5.0 | — | 12.0 |

-continued

|  | I | II | III | IV | V | VI |
|---|---|---|---|---|---|---|
| Mg sulfate | — | — | 0.1 | 0.2 | 0.2 | — |
| MA/AA | 0.5 | 1.6 | 3.0 | 4.0 | 1.0 | 1.0 |
| CMC | 0.2 | 0.4 | 1.0 | 1.0 | 0.4 | 0.4 |
| PB4 | 5.0 | 12.7 | — | — | — | — |
| Percarbonate | — | — | — | — | 18.0 | 15.0 |
| TAED | 0.5 | 3.1 | — | — | 5.0 | — |
| NACA-OBS | 1.0 | 3.5 | — | — | — | 2.5 |
| DETPMP | 0.25 | 0.2 | 0.3 | 0.4 | — | 0.2 |
| HEDP | — | 0.3 | — | 0.3 | 0.3 | 0.3 |
| QEA | — | — | 1.0 | 1.0 | 1.0 | — |
| CBD-transferase | 0.02 | 1.5 | 0.1 | 0.5 | 0.0008 | 0.02 |
| Substrate | — | 0.1 | 5.0 | 10.0 | 12.0 | 0.1 |
| Protease | 0.009 | 0.03 | 0.03 | 0.05 | 0.05 | 0.02 |
| Lipase | 0.003 | 0.003 | 0.006 | 0.006 | 0.006 | 0.004 |
| Cellulase | 0.0006 | 0.0006 | 0.0005 | 0.0005 | 0.0007 | 0.0007 |
| Amylase | 0.002 | 0.002 | 0.006 | 0.006 | 0.01 | 0.003 |
| PVNO/PVPVI | — | — | 0.2 | 0.2 | — | — |
| PVP | 0.9 | 1.3 | — | — | — | 0.9 |
| SRP 1 | — | — | 0.2 | 0.2 | 0.2 | — |
| Photoactivated bleach (ppm) | 15 | 27 | — | — | 20 | 20 |
| Photoactivated bleach 1 (ppm) | 15 | — | — | — | — | — |
| Brightener 1 | 0.08 | 0.2 | — | — | 0.09 | 0.15 |
| Brightener 2 | — | 0.04 | — | — | — | — |
| Perfume | 0.3 | 0.5 | 0.4 | 0.3 | 0.4 | 0.3 |
| Silicone antifoam | 0.5 | 2.4 | 0.3 | 0.5 | 0.3 | 2.0 |
| Density in g/liter | 750 | 750 | 750 | 750 | 750 | 750 |
| Miscellaneous and minors | | | Up to 100% | | | |

EXAMPLE 3

The following detergent compositions of particular utility under European machine wash conditions were prepared according to the present invention:

|  | I | II | III | IV |
|---|---|---|---|---|
| Blown Powder | | | | |
| LAS | 6.0 | 5.0 | 11.0 | 6.0 |
| TAS | 2.0 | — | — | 2.0 |
| Zeolite A | 24.0 | — | — | 20.0 |
| STPP | — | 27.0 | 24.0 | — |
| Sulfate | 4.0 | 6.0 | 13.0 | — |
| MA/AA | 1.0 | 4.0 | 6.0 | 2.0 |
| Silicate | 1.0 | 7.0 | 3.0 | 3.0 |
| CMC | 1.0 | 1.0 | 0.5 | 0.6 |
| Brightener 1 | 0.2 | 0.2 | 0.2 | 0.2 |
| Silicone antifoam | 1.0 | 1.0 | 1.0 | 0.3 |
| DETPMP | 0.4 | 0.4 | 0.2 | 0.4 |
| Spray On | | | | |
| Brightener | 0.02 | — | — | 0.02 |
| C45E7 | — | — | — | 5.0 |
| C45E2 | 2.5 | 2.5 | 2.0 | — |
| C45E3 | 2.6 | 2.5 | 2.0 | — |
| Perfume | 0.5 | 0.3 | 0.5 | 0.2 |
| Silicone antifoam | 0.3 | 0.3 | 0.3 | — |
| Dry additives | | | | |
| QEA | — | — | — | 1.0 |
| EDDS | 0.3 | — | — | — |
| Sulfate | 2.0 | 3.0 | 5.0 | 10.0 |
| Carbonate | 6.0 | 13.0 | 15.0 | 14.0 |
| Citric | 2.5 | — | — | 2.0 |
| QAS 1 | 0.5 | — | — | 0.5 |
| Na-SKS-6 | 10.0 | — | — | — |
| Percarbonate | 18.5 | — | — | — |
| PB4 | — | 18.0 | 10.0 | 21.5 |
| TAED | 2.0 | 2.0 | — | 2.0 |
| NACA-OBS | 3.0 | 2.0 | 4.0 | — |
| CBD-transferase | 0.005 | 1.0 | 0.1 | 0.2 |
| Substrate | — | 0.1 | 10.0 | 10.0 |
| Protease | 0.03 | 0.03 | 0.03 | 0.03 |
| Lipase | 0.008 | 0.008 | 0.008 | 0.004 |
| Amylase | 0.003 | 0.003 | 0.003 | 0.006 |
| Brightener 1 | 0.05 | — | — | 0.05 |
| Miscellaneous and minors | | Up to 100% | | |

EXAMPLE 4

The following granular detergent compositions were prepared according to the present invention:

|  | I | II | III | IV | V | VI |
|---|---|---|---|---|---|---|
| Blown Powder | | | | | | |
| LAS | 23.0 | 8.0 | 7.0 | 9.0 | 7.0 | 7.0 |
| TAS | — | — | — | — | 1.0 | — |
| C45AS | 6.0 | 6.0 | 5.0 | 8.0 | — | — |
| C45AES | — | 1.0 | 1.0 | 1.0 | — | — |
| C45E35 | — | — | — | — | 2.0 | 4.0 |
| Zeolite A | 10.0 | 18.0 | 14.0 | 12.0 | 10.0 | 10.0 |
| MA/AA | — | 0.5 | — | — | — | 2.0 |
| MA/AA 1 | 7.0 | — | — | — | — | — |
| AA | — | 3.0 | 3.0 | 2.0 | 3.0 | 3.0 |
| Sulfate | 5.0 | 6.3 | 14.3 | 11.0 | 15.0 | 19.3 |
| Silicate | 10.0 | 1.0 | 1.0 | 1.0 | 1.0 | 1.0 |
| Carbonate | 15.0 | 20.0 | 10.0 | 20.7 | 8.0 | 6.0 |

-continued

|  | I | II | III | IV | V | VI |
|---|---|---|---|---|---|---|
| PEG 4000 | 0.4 | 1.5 | 1.5 | 1.0 | 1.0 | 1.0 |
| DTPA | — | 0.9 | 0.5 | — | — | 0.5 |
| Brightener 2 | 0.3 | 0.2 | 0.3 | — | 0.1 | 0.3 |
| Spray On | | | | | | |
| C45E7 | — | 2.0 | — | — | 2.0 | 2.0 |
| C25E9 | 3.0 | — | — | — | — | — |
| C23E9 | — | — | 1.5 | 2.0 | — | 2.0 |
| Perfume | 0.3 | 0.3 | 0.3 | 2.0 | 0.3 | 0.3 |
| Agglomerates | | | | | | |
| C45AS | — | 5.0 | 5.0 | 2.0 | — | 5.0 |
| LAS | — | 2.0 | 2.0 | — | — | 2.0 |
| Zeolite A | — | 7.5 | 7.5 | 8.0 | — | 7.5 |
| Carbonate | — | 4.0 | 4.0 | 5.0 | — | 4.0 |
| PEG 4000 | — | 0.5 | 0.5 | — | — | 0.5 |
| Misc (Water etc.) | — | 2.0 | 2.0 | 2.0 | — | 2.0 |
| Dry additives | | | | | | |
| QAS | — | — | — | — | 1.0 | — |
| Citric | — | — | — | — | 2.0 | — |
| PB4 | — | — | — | — | 12.0 | 1.0 |
| PB1 | 4.0 | 1.0 | 3.0 | 2.0 | — | — |
| Percarbonate | — | — | — | — | 2.0 | 10.0 |
| Carbonate | — | 5.3 | 1.8 | — | 4.0 | 4.0 |
| NOBS | 4.0 | — | 6.0 | — | — | 0.6 |
| Methyl cellulose | 0.2 | — | — | — | — | — |
| Na-SKS-6 | 8.0 | — | — | — | — | — |
| STS | — | — | 2.0 | — | 1.0 | — |
| Culmene sulfonic acid | — | 1.0 | — | — | — | 2.0 |
| CBD-transferase | 0.025 | 0.8 | 0.5 | 0.01 | 0.025 | 0.8 |
| Substrate | — | 0.1 | 10.0 | 5.0 | 0.02 | — |
| Protease | 0.02 | 0.02 | 0.02 | 0.01 | 0.02 | 0.02 |
| Lipase | 0.004 | — | 0.004 | — | 0.004 | 0.008 |
| Amylase | 0.003 | — | 0.002 | — | 0.003 | — |
| Cellulase | 0.0005 | 0.0005 | 0.0005 | 0.0007 | 0.0005 | 0.0005 |
| PVPVI | — | — | — | — | 0.5 | 0.1 |
| PVP | — | — | — | — | 0.5 | — |
| PVNO | — | — | 0.5 | 0.3 | — | — |
| QEA | — | — | — | — | 1.0 | — |
| SRP 1 | 0.2 | 0.5 | 0.3 | — | 0.2 | — |
| Silicone antifoam | 0.2 | 0.4 | 0.2 | 0.4 | 0.1 | — |
| Mg sulfate | — | — | 0.2 | — | 0.2 | — |
| Miscellaneous and minors | Up to 100% | | | | | |

EXAMPLE 5

The following nil bleach-containing detergent compositions of particular use in the washing of coloured clothing were prepared according to the present invention:

|  | I | II | III |
|---|---|---|---|
| Blown Powder | | | |
| Zeolite A | 15.0 | 15.0 | — |
| Sulfate | — | 5.0 | — |
| LAS | 3.0 | 3.0 | — |
| DETPMP | 0.4 | 0.5 | — |
| CMC | 0.4 | 0.4 | — |
| MA/AA | 4.0 | 4.0 | — |
| Agglomerates | | | |
| C45AS | — | — | 11.0 |
| LAS | 6.0 | 5.0 | — |
| TAS | 3.0 | 2.0 | — |
| Silicate | 4.0 | 4.0 | — |
| Zeolite A | 10.0 | 15.0 | 13.0 |
| CMC | — | — | 0.5 |
| MA/AA | — | — | 2.0 |
| Carbonate | 9.0 | 7.0 | 7.0 |
| Spray-on | | | |
| Perfume | 0.3 | 0.3 | 0.5 |
| C45E7 | 4.0 | 4.0 | 4.0 |
| C25E3 | 2.0 | 2.0 | 2.0 |
| Dry additives | | | |
| MA/AA | — | — | 3.0 |
| Na-SKS-6 | — | — | 12.0 |
| Citrate | 10.0 | — | 8.0 |
| Bicarbonate | 7.0 | 3.0 | 5.0 |
| Carbonate | 8.0 | 5.0 | 7.0 |
| PVPVI/PVNO | 0.5 | 0.5 | 0.5 |
| CBD-transferase | 0.001 | 1.0 | 0.01 |
| Substrate | 0.1 | — | 5.0 |
| Protease | 0.03 | 0.02 | 0.05 |
| Lipase | 0.008 | 0.008 | 0.008 |
| Amylase | 0.01 | 0.01 | 0.01 |
| Cellulase | 0.001 | 0.001 | 0.001 |
| Silicone antifoam | 5.0 | 5.0 | 5.0 |
| Sulfate | — | 9.0 | — |
| Density (g/liter) | 700 | 700 | 700 |
| Miscellaneous and minors | Up to 100% | | |

EXAMPLE 6

The following detergent compositions were prepared according to the present invention:

|  | I | II | III | IV |
|---|---|---|---|---|
| Base granule | | | | |
| Zeolite A | 30.0 | 22.0 | 24.0 | 10.0 |
| Sulfate | 10.0 | 5.0 | 10.0 | 7.0 |
| MA/AA | 3.0 | — | — | — |
| AA | — | 1.6 | 2.0 | — |
| MA/AA 1 | — | 12.0 | — | 6.0 |
| LAS | 14.0 | 10.0 | 9.0 | 20.0 |
| C45AS | 8.0 | 7.0 | 9.0 | 7.0 |
| C45AES | — | 1.0 | 1.0 | — |
| Silicate | — | 1.0 | 0.5 | 10.0 |
| Soap | — | 2.0 | — | — |
| Brightener 1 | 0.2 | 0.2 | 0.2 | 0.2 |
| Carbonate | 6.0 | 9.0 | 10.0 | 10.0 |
| PEG 4000 | — | 1.0 | 1.5 | — |
| DTPA | — | 0.4 | — | — |
| Spray On | | | | |
| C25E9 | — | — | — | 5.0 |
| C45E7 | 1.0 | 1.0 | — | — |
| C23E9 | — | 1.0 | 2.5 | — |
| Perfume | 0.2 | 0.3 | 0.3 | — |
| Dry additives | | | | |
| Carbonate | 5.0 | 10.0 | 18.0 | 8.0 |
| PVPVI/PVNO | 0.5 | — | 0.3 | — |
| CBD-transferase | 1.0 | 0.01 | 0.5 | 0.1 |
| Substrate | 0.1 | — | 10.0 | 10.0 |
| Protease | 0.03 | 0.03 | 0.03 | 0.02 |
| Lipase | 0.008 | — | — | 0.008 |
| Amylase | 0.002 | — | — | 0.002 |
| Cellulase | 0.0002 | 0.0005 | 0.0005 | 0.0002 |
| NOBS | — | 4.0 | — | 4.5 |
| PB1 | 1.0 | 5.0 | 1.5 | 6.0 |
| Sulfate | 4.0 | 5.0 | — | 5.0 |

-continued

|  | I | II | III | IV |
|---|---|---|---|---|
| SRP 1 | — | 0.4 | — | — |
| Suds suppressor | — | 0.5 | 0.5 | — |
| Miscellaneous and minors | | Up to 100% | | |

EXAMPLE 7

The following granular detergent compositions were prepared according to the present invention:

|  | I | II | III |
|---|---|---|---|
| Blown Powder | | | |
| Zeolite A | 20.0 | — | 15.0 |
| STPP | — | 20.0 | — |
| Sulfate | — | — | 5.0 |
| Carbonate | — | — | 5.0 |
| TAS | — | — | 1.0 |
| LAS | 6.0 | 6.0 | 6.0 |
| C68AS | 2.0 | 2.0 | — |
| Silicate | 3.0 | 8.0 | — |
| MA/AA | 4.0 | 2.0 | 2.0 |
| CMC | 0.6 | 0.6 | 0.2 |
| Brightener 1 | 0.2 | 0.2 | 0.1 |
| DETPMP | 0.4 | 0.4 | 0.1 |
| STS | — | — | 1.0 |
| Spray On | | | |
| C45E7 | 5.0 | 5.0 | 4.0 |
| Silicone antifoam | 0.3 | 0.3 | 0.1 |
| Perfume | 0.2 | 0.2 | 0.3 |
| Dry additives | | | |
| QEA | — | — | 1.0 |
| Carbonate | 14.0 | 9.0 | 10.0 |
| PB1 | 1.5 | 2.0 | — |
| PB4 | 18.5 | 13.0 | 13.0 |
| TAED | 2.0 | 2.0 | 2.0 |
| QAS | — | — | 1.0 |
| Photoactivated bleach | 15 ppm | 15 ppm | 15 ppm |
| Na-SKS-6 | — | — | 3.0 |
| CBD-transferase | 0.001 | 1.0 | 0.01 |
| Substrate | — | — | 5.0 |
| Protease | 0.03 | 0.03 | 0.007 |
| Lipase | 0.004 | 0.004 | 0.004 |
| Amylase | 0.006 | 0.006 | 0.003 |
| Cellulase | 0.0002 | 0.0002 | 0.0005 |
| Sulfate | 10.0 | 20.0 | 5.0 |
| Density (g/liter) | 700 | 700 | 700 |
| Miscellaneous and minors | | Up to 100% | |

EXAMPLE 8

The following detergent compositions were prepared according to the present invention:

|  | I | II | III |
|---|---|---|---|
| Blown Powder | | | |
| Zeolite A | 15.0 | 15.0 | 15.0 |
| Sulfate | — | 5.0 | — |
| LAS | 3.0 | 3.0 | 3.0 |
| QAS | — | 1.5 | 1.5 |
| DETPMP | 0.4 | 0.2 | 0.4 |
| EDDS | — | 0.4 | 0.2 |

-continued

|  | I | II | III |
|---|---|---|---|
| CMC | 0.4 | 0.4 | 0.4 |
| MA/AA | 4.0 | 2.0 | 2.0 |
| Agglomerate | | | |
| LAS | 5.0 | 5.0 | 5.0 |
| TAS | 2.0 | 2.0 | 1.0 |
| Silicate | 3.0 | 3.0 | 4.0 |
| Zeolite A | 8.0 | 8.0 | 8.0 |
| Carbonate | 8.0 | 8.0 | 4.0 |
| Spray On | | | |
| Perfume | 0.3 | 0.3 | 0.3 |
| C45E7 | 2.0 | 2.0 | 2.0 |
| C25E3 | 2.0 | — | — |
| Dry Additives | | | |
| Citrate | 5.0 | — | 2.0 |
| Bicarbonate | — | 3.0 | — |
| Carbonate | 8.0 | 15.0 | 10.0 |
| TAED | 6.0 | 2.0 | 5.0 |
| PB1 | 14.0 | 7.0 | 10.0 |
| PEO | — | — | 0.2 |
| Bentonite clay | — | — | 10.0 |
| CBD-transferase | 0.025 | 0.5 | 0.1 |
| Substrate | 0.01 | — | 12.0 |
| Protease | 0.03 | 0.03 | 0.03 |
| Lipase | 0.008 | 0.008 | 0.008 |
| Cellulase | 0.001 | 0.001 | 0.001 |
| Amylase | 0.01 | 0.01 | 0.01 |
| Silicone antifoam | 5.0 | 5.0 | 5.0 |
| Sulfate | — | 3.0 | — |
| Density (g/liter) | 850 | 850 | 850 |
| Miscellaneous and minors | | Up to 100% | |

EXAMPLE 9

The following detergent compositions were prepared according to the present invention:

|  | I | II | III | IV |
|---|---|---|---|---|
| LAS | 18.0 | 14.0 | 24.0 | 20.0 |
| QAS | 0.7 | 1.0 | — | 0.7 |
| TFAA | — | 1.0 | — | — |
| C23E56.5 | — | — | 1.0 | — |
| C45E7 | — | 1.0 | — | — |
| C45E3S | 1.0 | 2.5 | 1.0 | — |
| STPP | 32.0 | 18.0 | 30.0 | 22.0 |
| Silicate | 9.0 | 5.0 | 9.0 | 8.0 |
| Carbonate | 11.0 | 7.5 | 10.0 | 5.0 |
| Bicarbonate | — | 7.5 | — | — |
| PB1 | 3.0 | 1.0 | — | — |
| PB4 | — | 1.0 | — | — |
| NOBS | 2.0 | 1.0 | — | — |
| DETPMP | — | 1.0 | — | — |
| DTPA | 0.5 | — | 0.2 | 0.3 |
| SRP 1 | 0.3 | 0.2 | — | 0.1 |
| MA/AA | 1.0 | 1.5 | 2.0 | 0.5 |
| CMC | 0.8 | 0.4 | 0.4 | 0.2 |
| PEI | — | — | 0.4 | — |
| Sulfate | 20.0 | 10.0 | 20.0 | 30.0 |
| Mg sulfate | 0.2 | — | 0.4 | 0.9 |
| CBD-transferase | 0.001 | 0.5 | 0.01 | 0.5 |
| Substrate | — | 0.05 | 5.0 | 10.0 |
| Protease | 0.03 | 0.03 | 0.02 | 0.02 |
| Amylase | 0.008 | 0.007 | — | 0.004 |
| Lipase | 0.004 | — | 0.002 | — |
| Cellulase | 0.0003 | — | — | 0.0001 |
| Photoactivated bleach | 30 ppm | 20 ppm | — | 10 ppm |
| Perfume | 0.3 | 0.3 | 0.1 | 0.2 |
| Brightener 1/2 | 0.05 | 0.02 | 0.08 | 0.1 |
| Miscellaneous and minors | | up to 100% | | |

EXAMPLE 10

The following liquid detergent formulations were prepared according to the present invention (Levels are given in parts per weight, enzyme are expressed in pure enzyme):

|  | I | II | III | IV | V |
|---|---|---|---|---|---|
| LAS | 11.5 | 8.8 | — | 3.9 | — |
| C25E2.5S | — | 3.0 | 18.0 | — | 16.0 |
| C45E2.25S | 11.5 | 3.0 | — | 15.7 | — |
| C23E9 | — | 2.7 | 1.8 | 2.0 | 1.0 |
| C23E7 | 3.2 | — | — | — | — |
| CFAA | — | — | 5.2 | — | 3.1 |
| TPKFA | 1.6 | — | 2.0 | 0.5 | 2.0 |
| Citric (50%) | 6.5 | 1.2 | 2.5 | 4.4 | 2.5 |
| Ca formate | 0.1 | 0.06 | 0.1 | — | — |
| Na formate | 0.5 | 0.06 | 0.1 | 0.05 | 0.05 |
| SCS | 4.0 | 1.0 | 3.0 | 1.2 | — |
| Borate | 0.6 | — | 3.0 | 2.0 | 2.9 |
| Na hydroxide | 5.8 | 2.0 | 3.5 | 3.7 | 2.7 |
| Ethanol | 1.75 | 1.0 | 3.6 | 4.2 | 2.9 |
| 1,2 Propanediol | 3.3 | 2.0 | 8.0 | 7.9 | 5.3 |
| Monoethanolamine | 3.0 | 1.5 | 1.3 | 2.5 | 0.8 |
| TEPAE | 1.6 | — | 1.3 | 1.2 | 1.2 |
| CBD-transferase | 0.001 | 0.01 | 1.0 | 0.05 | 0.5 |
| Substrate | 0.1 | — | 0.01 | — | 10.0 |
| Protease | 0.03 | 0.01 | 0.03 | 0.02 | 0.02 |
| Lipase | — | — | 0.002 | — | — |
| Amylase | — | — | — | 0.002 | — |
| Cellulase | — | — | 0.0002 | 0.0005 | 0.0001 |
| SRP 1 | 0.2 | — | 0.1 | — | — |
| DTPA | — | — | 0.3 | — | — |
| PVNO | — | — | 0.3 | — | 0.2 |
| Brightener 1 | 0.2 | 0.07 | 0.1 | — | — |
| Silicone antifoam | 0.04 | 0.02 | 0.1 | 0.1 | 0.1 |
| Miscellaneous and water |  |  |  |  |  |

EXAMPLE 11

The following liquid detergent formulations were prepared according to the present invention (Levels are given in parts per weight, enzyme are expressed in pure enzyme):

|  | I | II | III | IV |
|---|---|---|---|---|
| LAS | 10.0 | 13.0 | 9.0 | — |
| C25AS | 4.0 | 1.0 | 2.0 | 10.0 |
| C25E3S | 1.0 | — | — | 3.0 |
| C25E7 | 6.0 | 8.0 | 13.0 | 2.5 |
| TFAA | — | — | — | 4.5 |
| APA | — | 1.4 | — | — |
| TPKFA | 2.0 | — | 13.0 | 7.0 |
| Citric | 2.0 | 3.0 | 1.0 | 1.5 |
| Dodecenyl/tetradecenyl succinic acid | 12.0 | 10.0 | — | — |
| Rapeseed fatty acid | 4.0 | 2.0 | 1.0 | — |
| Ethanol | 4.0 | 4.0 | 7.0 | 2.0 |
| 1,2 Propanediol | 4.0 | 4.0 | 2.0 | 7.0 |
| Monoethanolamine | — | — | — | 5.0 |
| Triethanolamine | — | — | 8.0 | — |
| TEPAE | 0.5 | — | 0.5 | 0.2 |
| DETPMP | 1.0 | 1.0 | 0.5 | 1.0 |
| CBD-transferase | 0.01 | 0.01 | 0.01 | 0.001 |
| Substrate | 5.0 | — | 5.0 | 0.1 |
| Protease | 0.02 | 0.02 | 0.01 | 0.008 |
| Lipase | — | 0.002 | — | 0.002 |
| Amylase | 0.004 | 0.004 | 0.01 | 0.008 |
| Cellulase | — | — | — | 0.002 |
| SRP 2 | 0.3 | — | 0.3 | 0.1 |
| Boric acid | 0.1 | 0.2 | 1.0 | 2.0 |
| Ca chloride | — | 0.02 | — | 0.01 |
| Brightener 1 | — | 0.4 | — | — |
| Suds suppressor | 0.1 | 0.3 | — | 0.1 |
| Opacifier | 0.5 | 0.4 | — | 0.3 |
| NaOH up to pH | 8.0 | 8.0 | 7.6 | 7.7 |
| Miscellaneous and water |  |  |  |  |

EXAMPLE 12

The following liquid detergent compositions were prepared according to the present invention (Levels are given in parts per weight, enzyme are expressed in pure enzyme):

|  | I | II | III | IV |
|---|---|---|---|---|
| LAS | 25.0 | — | — | — |
| C25AS | — | 13.0 | 18.0 | 15.0 |
| C25E3S | — | 2.0 | 2.0 | 4.0 |
| C25E7 | — | — | 4.0 | 4.0 |
| TFAA | — | 6.0 | 8.0 | 8.0 |
| APA | 3.0 | 1.0 | 2.0 | — |
| TPKFA | — | 15.0 | 11.0 | 11.0 |
| Citric | 1.0 | 1.0 | 1.0 | 1.0 |
| Dodecenyl/tetradecenyl succinic acid | 15.0 | — | — | — |
| Rapeseed fatty acid | 1.0 | — | 3.5 | — |
| Ethanol | 7.0 | 2.0 | 3.0 | 2.0 |
| 1,2 Propanediol | 6.0 | 8.0 | 10.0 | 13.0 |
| Monoethanolamine | — | — | 9.0 | 9.0 |
| TEPAE | — | — | 0.4 | 0.3 |
| DETPMP | 2.0 | 1.2 | 1.0 | — |
| CBD-transferase | 0.01 | 1.0 | 0.05 | 0.5 |
| Substrate | 5.0 | 0.01 | — | 10.0 |
| Protease | 0.08 | 0.02 | 0.01 | 0.02 |
| Lipase | — | — | 0.003 | 0.003 |
| Amylase | 0.004 | 0.01 | 0.01 | 0.01 |
| Cellulase | — | — | 0.004 | 0.003 |
| SRP 2 | — | — | 0.2 | 0.1 |
| Boric acid | 1.0 | 1.5 | 2.5 | 2.5 |
| Bentonite clay | 4.0 | 4.0 | — | — |
| Brightener 1 | 0.1 | 0.2 | 0.3 | — |
| Suds suppressor | 0.4 | — | — | — |
| Opacifier | 0.8 | 0.7 | — | — |
| NaOH up to pH | 8.0 | 7.5 | 8.0 | 8.2 |
| Miscellaneous and water |  |  |  |  |

EXAMPLE 13

The following liquid detergent compositions were prepared according to the present invention (Levels are given in parts by weight, enzyme are expressed in pure enzyme):

|  | I | II |
|---|---|---|
| LAS | 27.6 | 18.9 |
| C45AS | 13.8 | 5.9 |
| C13E8 | 3.0 | 3.1 |
| Oleic acid | 3.4 | 2.5 |
| Citric | 5.4 | 5.4 |
| Na hydroxide | 0.4 | 3.6 |
| Ca Formate | 0.2 | 0.1 |
| Na Formate | — | 0.5 |
| Ethanol | 7.0 | — |
| Monoethanolamine | 16.5 | 8.0 |
| 1,2 propanediol | 5.9 | 5.5 |
| Xylene sulfonic acid | — | 2.4 |
| TEPAE | 1.5 | 0.8 |
| Protease | 0.05 | 0.02 |
| CBD-transferase | 0.05 | 0.5 |

-continued

|  | I | II |
|---|---|---|
| Substrate | — | 10.0 |
| PEG | — | 0.7 |
| Brightener 2 | 0.4 | 0.1 |
| Perfume | 0.5 | 0.3 |
| Water and Minors | | |

EXAMPLE 14

The following granular fabric detergent compositions which provide "softening through the wash" capability were prepared according to the present invention:

|  | I | II |
|---|---|---|
| C45AS | — | 10.0 |
| LAS | 7.6 | — |
| C68AS | 1.3 | — |
| C45E7 | 4.0 | — |
| C25E3 | — | 5.0 |
| Coco-alkyl-dimethyl hydroxy-ethyl ammonium chloride | 1.4 | 1.0 |
| Citrate | 5.0 | 3.0 |
| Na-SKS-6 | — | 11.0 |
| Zeolite A | 15.0 | 15.0 |
| MA/AA | 4.0 | 4.0 |
| DETPMP | 0.4 | 0.4 |
| PB1 | 15.0 | — |
| Percarbonate | — | 15.0 |
| TAED | 5.0 | 5.0 |
| Smectite clay | 10.0 | 10.0 |
| HMWPEO | — | 0.1 |
| CBD-transferase | 0.001 | 0.01 |
| Substrate | — | 5.0 |
| Protease | 0.02 | 0.01 |
| Lipase | 0.02 | 0.01 |
| Amylase | 0.03 | 0.005 |
| Cellulase | 0.001 | — |
| Silicate | 3.0 | 5.0 |
| Carbonate | 10.0 | 10.0 |
| Suds suppressor | 1.0 | 4.0 |
| CMC | 0.2 | 0.1 |
| Miscellaneous and minors | Up to 100% | |

EXAMPLE 15

The following rinse added fabric softener composition was prepared according to the present invention:

| DEQA (2) | 20.0 |
|---|---|
| CBD-transferase | 0.5 |
| Substrate | 0.1 |
| Cellulase | 0.001 |
| HCL | 0.03 |
| Antifoam agent | 0.01 |
| Blue dye | 25 ppm |
| CaCl$_2$ | 0.20 |
| Preservatives | 0.05 |
| Perfume | 0.90 |
| Miscellaneous and water | Up to 100% |

EXAMPLE 16

The following fabric softener and dryer added fabric conditioner compositions were prepared according to the present invention:

|  | I | II | III | IV | V |
|---|---|---|---|---|---|
| DEQA | 2.6 | 19.0 | — | — | — |
| DEQA(2) | — | — | — | — | 51.8 |
| DTMAMS | — | — | — | 26.0 | — |
| SDASA | — | — | 70.0 | 42.0 | 40.2 |
| Stearic acid of IV = 0 | 0.3 | — | — | — | — |
| Neodol 45-13 | — | — | 13.0 | — | — |
| Hydrochloride acid | 0.02 | 0.02 | — | — | — |
| Ethanol | — | — | 1.0 | — | — |
| CBD-transferase | 0.001 | 0.5 | 0.01 | 0.1 | 0.001 |
| Substrate | — | 0.1 | 5.0 | 5.0 | 1.0 |
| Perfume | 1.0 | 1.0 | 0.75 | 1.0 | 1.5 |
| Glycoperse S-20 | — | — | — | — | 15.4 |
| Glycerol monostearate | — | — | — | 26.0 | — |
| Digeranyl Succinate | — | — | 0.38 | — | — |
| Silicone antifoam | 0.01 | 0.01 | — | — | — |
| Electrolyte | — | 0.1 | — | — | — |
| Clay | — | — | — | 3.0 | — |
| Preservatives | 0.05 | 0.05 | — | — | — |
| Dye | 10 ppm | 25 ppm | 0.01 | — | — |
| Water and minors | 100% | 100% | — | — | — |

EXAMPLE 17

The following laundry bar detergent compositions were prepared according to the present invention (Levels are given in parts per weight, enzyme are expressed in pure enzyme):

|  | I | II | III | VI | V | III | VI | V |
|---|---|---|---|---|---|---|---|---|
| LAS | — | — | 19.0 | 15.0 | 21.0 | 6.75 | 8.8 | — |
| C28AS | 30.0 | 13.5 | — | — | — | 15.75 | 11.2 | 22.5 |
| Na Laurate | 2.5 | 9.0 | — | — | — | — | — | — |
| Zeolite A | 2.0 | 1.25 | — | — | — | 1.25 | 1.25 | 1.25 |
| Carbonate | 20.0 | 3.0 | 13.0 | 8.0 | 10.0 | 15.0 | 15.0 | 10.0 |
| Ca Carbonate | 27.5 | 39.0 | 35.0 | — | — | 40.0 | — | 40.0 |
| Sulfate | 5.0 | 5.0 | 3.0 | 5.0 | 3.0 | — | — | 5.0 |
| TSPP | 5.0 | — | — | — | — | 5.0 | 2.5 | — |
| STPP | 5.0 | 15.0 | 10.0 | — | — | 7.0 | 8.0 | 10.0 |
| Bentonite clay | — | 10.0 | — | — | 5.0 | — | — | — |
| DETPMP | — | 0.7 | 0.6 | — | 0.6 | 0.7 | 0.7 | 0.7 |
| CMC | — | 1.0 | 1.0 | 1.0 | 1.0 | — | — | 1.0 |
| Talc | — | — | 10.0 | 15.0 | 10.0 | — | — | — |
| Silicate | — | — | 4.0 | 5.0 | 3.0 | — | — | — |
| PVNO | 0.02 | 0.03 | — | 0.01 | — | 0.02 | — | — |
| MA/AA | 0.4 | 1.0 | — | — | 0.2 | 0.4 | 0.5 | 0.4 |
| SRP 1 | 0.3 | 0.3 | 0.3 | 0.3 | 0.3 | 0.3 | 0.3 | 0.3 |
| CBD-transferase | 0.001 | 0.05 | 0.5 | 0.01 | 0.001 | 0.05 | 0.5 | 0.01 |
| Substrate | 0.1 | 5.0 | 8.0 | 5.0 | — | 0.1 | 2.0 | 5.0 |
| Amylase | — | — | 0.01 | — | — | — | 0.002 | — |
| Protease | — | 0.004 | — | 0.003 | 0.003 | — | — | 0.003 |
| Lipase | — | 0.002 | — | 0.002 | — | — | — | — |
| Cellulase | — | .0003 | — | — | .0003 | .0002 | — | — |
| PEO | — | 0.2 | — | 0.2 | 0.3 | — | — | 0.3 |
| Perfume | 1.0 | 0.5 | 0.3 | 0.2 | 0.4 | — | — | 0.4 |
| Mg sulfate | — | — | 3.0 | 3.0 | 3.0 | — | — | — |
| Brightener | 0.15 | 0.1 | 0.15 | — | — | — | — | 0.1 |
| Photo activated bleach (ppm) | — | 15.0 | 15.0 | 15.0 | 15.0 | — | — | 15.0 |

EXAMPLE 18

The following pre- or post treatment compositions were prepared in accord with the present invention:

|  | I | II | III | IV | V | VI |
|---|---|---|---|---|---|---|
| DEQA (2) | — | — | 20.0 | — | 20.0 | 20.0 |
| CBD-transferase | 0.8 | 0.05 | 0.05 | 0.005 | 0.05 | 0.15 |
| Substrate | — | 10.0 | 10.0 | 1.0 | 0.1 | 5.0 |
| Cellulase | — | — | 0.001 | — | 0.001 | 0.001 |
| HCL | — | — | 0.03 | — | 0.03 | 0.03 |
| Antifoam agent | — | — | 0.01 | — | 0.01 | 0.01 |
| Blue dye | 25 ppm | 25 ppm | 25 ppm | 25 ppm | 25 ppm | 25 ppm |
| CaCl$_2$ | — | — | 0.20 | — | 0.20 | 0.20 |
| Preservatives | 0.05 | 0.05 | 0.05 | 0.05 | 0.05 | 0.05 |
| Perfume | 0.90 | 0.90 | 0.90 | 0.90 | 0.90 | 0.90 |
| Water/minors | Up to 100% | | | | | |

What is claimed is:

1. A modified enzyme which comprises a catalytically active amino acid sequence of a transferase linked to an amino acid sequence comprising a cellulose binding domain via a linking region selected from the group consisting of, Humicola insolens family 45 cellulase linker, NifA gene of Klebsiella pneumonia-CiP linker, E. coli OmpA gene-CiP linker, E3 cellulase Thermomonospora fusca linker, CenA cellulase linker, polyethylene glycol derivatives, 1-ethyl-3-(3-dimethylaminopropyl) carbodiimide, N-ethyl-5-phenylisoaxolium-3-sulphonate, N-ethoxycarbonyl-2-ethoxy 1,2,dihydroquinoline or glutaraldehyde, crosslinkers and combinations thereof; wherein said transferase is selected from the group consisting of: EC 2.1.1.15, EC 2.1.1.18, EC 2.1.2.1, EC 2.1.2.4, EC 2.2.1.3, EC 2.3.1.3, EC 2.3.1.18, EC 2.3.1.57, EC 2.3.1.75, EC 2.3.1.79, EC 2.3.1.84, EC 2.3.1.88, EC 2.3.1.96, EC 2.3.1.142, EC 2.4.1.2, EC 2.4.1.4, EC 2.4.1.5, EC 2.4.1.9, EC 2.4.1.10, EC 2.4.1.11, EC 2.4.1.12, EC 2.4.1.13, EC 2.4.1.16, EC 2.4.1.18, EC 2.4.1.21, EC 2.4.1 24, EC 2.4.1.25, EC 2.4.1.29, EC 2.4.1.34, EC 2.4.1.35, EC 2.4.1.49, EC 2.4.1.67, EC 2.4.1.71, EC 2.4.1.75, EC 2.4.1.82, EC 2.4.1.90, EC 2.4.1.93, EC 2.4.1.99, EC 2.4.1.100, EC 2.4.1.113, EC 2.4.1.121, EC 2.4.1.125, EC 2.4.1.140, EC 2.4.1.161, EC 2.4.1.168, EC 2.4.1.169, EC 2.4.1.183, EC 2.5.1.10, EC 2.5.1.20, EC 2.6.1, 2.3.2.13, xyloglucan endotransglycosylase (XET), endo-xyloglucan transferase (EXGT) and combinations thereof.

2. A modified enzyme according to claim 1 wherein said transferase is selected from the group consisting of a transglucosidase (EC 2.4.1.24), an endoxyloglucan transferase, an alternansucrase (EC 2.4.1.140) and mixtures thereof.

3. A modified enzyme according to claim 2 wherein said transferase is a dextransucrase (EC 2.4.1.5).

4. A modified enzyme according to claim 1 wherein said modified enzyme has at least 50% of its maximum activity between 10° C. and 50° C.

5. A modified enzyme according to claim 1 wherein said modified enzyme is alkaline.

6. A modified enzyme according to claim 1 wherein said cellulose binding domain is selected from the group consisting of CBD CenC, CenA, Cex from Cellulomonas fimi, CBD CBHI from Trichoderma reesei, CBD Cellulozome from Clostridium cellulovorans, CBD E3 from Thermonospora fusca, CBD-dimer from Clostridium stecorarium XynA, CBD from Bacillus agaradherens, CBD family 45 from Humicola insolens and mixtures thereof.

7. A modified enzyme according to claim 6 wherein said cellulose binding domain is selected from the group consisting of CBD family 45 from Humicola insolens, CBD CenC from Cellulomonas fimi, CBD Cellulozome from Clostridium cellulovorans and mixtures thereof.

8. A modified enzyme according to claim 1 further comprising a linking region between the catalytically active amino acid sequence of a transferase enzyme and the amino acid sequence comprising a cellulose binding domain.

9. A modified enzyme according to claim 8 wherein the linking region is an amino acid linking region.

10. A modified enzyme according to claim 8 wherein the linking region is a non-amino acid linking region.

11. A modified enzyme according to claim 10 wherein the linking region is a polymer selected from the group consisting of: PEG(NPC)2(NH2)2-PEG, t-BOC-NH-PEG-NH2, MAL-PEG-NHS, VS-PEG-NHS polymers and mixtures thereof.

12. A laundry detergent and/or fabric care composition comprising a laundry detergent and/or fabric care ingredient and a modified enzyme according to claim 1.

13. A laundry detergent and/or fabric care composition according to claim 12 wherein said modified enzyme is present at a level of from 0.0001% to 10% pure modified enzyme by weight of the composition.

14. A laundry detergent and/or fabric care composition according to claim 13 wherein said modified enzyme is present at a level of from 0.0005% to 5% pure modified enzyme by weight of the composition.

15. A laundry detergent and/or fabric care composition according to claim 14 wherein said modified enzyme is present at a level of from 0.001% to 1% pure modified enzyme by weight of the composition.

16. A laundry detergent and/or fabric care composition according to claim 12 further comprising a substrate for said modified enzyme.

17. A laundry detergent and/or fabric care composition according to claim 16 wherein said, substrate is present at a level of from 0.01% to 30% substrate by weight of the composition.

18. A laundry detergent and/or fabric care composition according to claim 17 wherein said substrate is present at a level of from 0. 1% to 20% substrate by weight of the composition.

19. A laundry detergent and/or fabric care composition according to claim 18 wherein said substrate is present at a level of from 1% to 10% substrate by weight of the composition.

20. A laundry detergent and/or fabric care composition according to claim 16 wherein said substrate is a glycosidic dimer, oligomer and/or polymer.

21. A laundry detergent and/or fabric care composition according to claim 20 wherein said substrate is selected from the group consisting of: starch, xyloglucan, cyclodextrin, sucrose, maltose and mixtures thereof.

22. A laundry detergent and/or fabric care composition according to claim 20 said substrate is selected from the group consisting of: an amino acid, a di/tri/poly-peptide, a protein and mixtures thereof.

23. A laundry detergent and/or fabric care composition according to claim 12 further comprising at least 5% by weight of the composition of an anionic surfactant.

24. A laundry detergent and/or fabric care composition according to claim 23 wherein said anionic surfactant is selected from the group consisting of: an alkyl sulfate an alkyl ethoxy sulfate, a linear alkylene sulfonate and mixtures thereof.

25. A laundry detergent and/or fabric care composition according to claim 12 further comprising at least 2% by weight of the composition of an alkyl ethoxylate nonionic surfactant.

26. A laundry detergent and/or fabric care composition according to claim 12 further comprising a laundry detergent and/or fabric care composition ingredient selected from the group consisting of: cationic surfactants, anionic surfactants, nonionic surfactants, detergent enzymes, bleaching agents, dye transfer inhibiting agents, dispersants, smectite clay and mixtures thereof.

27. A laundry detergent and/or fabric care composition according to claim 26 wherein said cationic surfactant comprises two long chain alkyl chain lengths.

28. A laundry detergent and/or fabric care composition according to claim 26 wherein said detergent enzymes are selected from the group consisting of: proteases, cellulases, lipases, amylases and mixtures thereof.

29. A laundry detergent and/or fabric care composition according to claim 12 wherein said composition is in the form of an additive, a pre-treatment, a post-treatment, a soaking treatment and/or a rinsing treatment composition.

30. A laundry detergent and/or fabric care composition according to claim 12 wherein said composition is in the form of a spray and/or foam.

31. A laundry detergent and/or fabric care composition according to claim 12 wherein said composition is in the form of a granular composition containing no more than 15% by weight of the composition of an inorganic filler salt.

32. A laundry detergent and/or fabric care composition according to claim 12 wherein said composition is in the form of a liquid composition containing no more than 40% by weight of the composition of water.

33. A laundry detergent and/or fabric care composition according to claim 32 wherein said composition contains no more than 30% by weight of the composition of water.

34. A laundry detergent and/or fabric care composition according to claim 33 wherein said composition contains no more than 20% by weight of the composition of water.

35. A method for refurbishing and/or restoring tensile strength and/or providing anti-wrinkle and/or anti-bobbling and/or anti-shrinkage and/or static control and/or fabric softness, and/or color appearance and/or fabric anti-wear properties to a fabric comprising contacting the fabric with a laundry detergent and/or fabric care composition according to claim 12 such that the fabric is treated.

36. A method according to claim 35 wherein said fabric is treated with an enzymatic substrate.

37. A method according to claim 35 wherein said fabric has been treated by a laundry and/or fabric care pre-treatment and/or post-treatment composition.

38. A modified enzyme which comprises a catalytically active amino acid sequence of a transferase linked to an amino acid sequence comprising a cellulose binding domain via a linking region selected from the group consisting of: *Humicola insolens* family 45 cellulase linker, NifA gene of *Klebsiella pneumoniae*-CiP linker, *E. coli* OmpA gene-CiP linker, E3 cellulase *Thermomonospora fusca* linker, CenA cellulase linker, polyethylene glycol derivatives, 1-ethyl-3-(3-dimethylaminopropyl) carbodiimide, N-ethyl-5-phenylisoaxolium-3-sulphonate, N-ethoxycarbonyl-2-ethoxy, 1,2 dihydroquinoline or glutaraldehyde, crosslinkers and combinations thereof; wherein said transferase is a mutant glycosyl transferase selected from the group consisting of: EC 2.4.1.2, EC 2.4.1.4, EC 2.4.1.5, EC 2.4.1.9, EC 2.4.1.10, EC 2.4. 1.11, EC 2.4.1.12, EC 2.4.1.13, EC 2.4.1.16, EC 2.4.1.18, EC 2.4.1.21, EC 2.4.1.24, EC 2.4.1.25, EC 2.4.1.29, EC 2.4.1.34, EC 2.4.1.35, EC 2.4.1.49, EC 2.4.1.67, EC 2.4.1.71, EC 2.4.1.75, EC 2.4.1.82, EC 2.4.1.90, EC 2.4.1.93, EC 2.4.1.99, EC 2.4.1.100, EC 2.4.1.113, EC 2.4.1.121, EC 2.4.1.125, EC 2.4.1.140, EC 2.4.1.161, EC 2.4.1.168, EC 2.4.1.168, EC 2.4.1.169, EC 2.4.1.183 and mixture thereof.

* * * * *